United States Patent [19]

Long et al.

[11] Patent Number: 5,453,423

[45] Date of Patent: Sep. 26, 1995

[54] HETEROCYCLIC AMINES USEFUL IN THE THERAPY OF ASTHMA AND IMFLAMMATION OF THE RESPIRATORY TRACT

[75] Inventors: Giorgio Long; Carmelo A. Gandolfi; Gianpiero De Cillis; Roberto Di Domenico; Antonella Rozzi; Licia Gallico, all of Milan, Italy

[73] Assignee: Boehringer Mannheim Italia S.p.A., Milan, Italy

[21] Appl. No.: 119,202

[22] PCT Filed: Apr. 1, 1992

[86] PCT No.: PCT/EP92/00724

§ 371 Date: Sep. 27, 1993

§ 102(e) Date: Sep. 27, 1993

[87] PCT Pub. No.: WO92/18478

PCT Pub. Date: Oct. 29, 1992

[30] Foreign Application Priority Data

Apr. 9, 1991 [IT] Italy .................... MI91A0966

[51] Int. Cl.$^6$ .................... A61K 31/505; A61K 31/495; C07D 241/04; C07D 239/28
[52] U.S. Cl. .................... 514/211; 514/227.8; 514/235.8; 514/252; 514/255; 540/544; 544/60; 544/121; 544/295; 544/360; 544/367; 544/372
[58] Field of Search .................... 544/60, 121, 295, 544/360, 367, 372; 514/227.8, 235.8, 252, 211, 255; 540/544

[56] References Cited

U.S. PATENT DOCUMENTS 5,332,735 7/1994 Rault et al. ................ 514/235.5

5,340,809 8/1994 Gandry et al. ................ 514/252

FOREIGN PATENT DOCUMENTS 0333080 9/1989 European Pat. Off. ..
0348541 1/1990 European Pat. Off. ..
0461012 11/1991 European Pat. Off. ..

OTHER PUBLICATIONS

WO, A, 8 908 648 (Boehringer Biochemica Robin) 21, Sep. 1989.

Chemical Abstracts, vol. 109, No. 19, 7 Nov. 1988, Abstract No. 170371.

Chemical Abstracts, vol. 97, No. 23, 6 Dec. 1982, Abstract No. 198218.

*Primary Examiner*—Mukund J. Shah
*Assistant Examiner*—Matthew V. Grumbling
*Attorney, Agent, or Firm*—Nikaido, Marmelstein, Murray & Oram

[57] ABSTRACT

Compounds of the formula

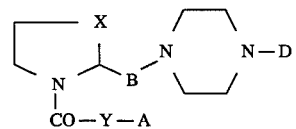

wherein A, Y, X, B and D are described in the specification are disclosed. The compounds possess activity in treating asthma and other pathologies of the respiratory tract.

7 Claims, No Drawings

HETEROCYCLIC AMINES USEFUL IN THE THERAPY OF ASTHMA AND IMFLAMMATION OF THE RESPIRATORY TRACT

This is the national stage of PCT/EP92/00724, filed Apr. 1, 1992.

The present invention relates to heterocyclic amines, a process for the preparation thereof and pharmaceutical compositions containing them.

More precisely, the invention relates to compounds of formula (I):

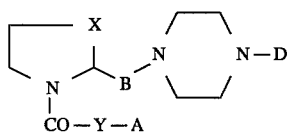

the single enantiomeric and diastereoisomeric forms thereof, the racemic mixtures thereof and the salts thereof with pharmaceutically acceptable acids and bases, wherein:

X is $CH_2$ or S;

B is a —CO—, —$CH_2$—, —$CH_2$OCO—, —$CH_2$OCS—, —$CH_2$NHCO—, or —$CH_2$NHCS— group;

D is a benzyl group which can optionally be substituted by hydroxy and/or $C_1$–$C_6$ alkoxy groups; benzhydryl optionally substituted by halogen atoms; phenyl optionally substituted by halogen atoms; (3-hydroxy-2-pyridyl)methyl; 5- or 6-membered heterocycle with 1–3 nitrogen atoms, which can possibly be substituted by 1 or 2 amino groups, mono-$C_1$–$C_6$-alkylamino, mono-$C_3$–$C_7$-alkenyl- or mono-$C_{3-C7}$-alkinylamino, di-$C_1$–$C_6$-alkylamino, ($C_{1-C6}$)alkyl($C_{3-C7}$)alkenylamino, piperidin-1-yl, morpholin-4-yl, pyrrolidin-1-yl;

Y is a single carbon-carbon bond or a group of formula

wherein Ra and Rb are hydrogen, $C_1$–$C_3$ alkyl or, taken together with the carbon atom which they are linked to, form a $C_3$–$C_6$ cycloalkyl group;

A is selected from the group consisting of:
a) a free or salified carboxy group, which can possibly be esterified with $C_1$–$C_4$ alkyl alcohols or amide, sulfonamide or hydroxyamido derivatives thereof, respectively of formulae CONRcRd, CONHSO₂Rf and CONRgOH, wherein Rc and Rd, which can be the same or different, are hydrogen, $C_1$–$C_6$ alkyl, benzyl, ortho-, meta- or para-aminopyridino, or, taken together with the nitrogen atom, form a pyrrolidino, piperidino, morpholino, 4-thiomorpholino, 4,5-dithiaazepino, $C_1$–$C_4$-4-alkylpiperazino, imidazolyl group; Rf is $C_1$–$C_4$-alkyl, trihalomethyl, tolyl or phenyl, possibly substituted by halogen atoms; Rg is H or $C_1$–$C_4$-alkyl;
b) $C_1$–$C_3$-alkyl;
c) NRcRd, wherein Rc and Rd are as defined above;
d) —CO—Rh, wherein Rh is $C_1$–$C_2$ alkyl optionally substituted by $C_5$–$C_6$ cycloalkyl or phenyl groups;
e) when Y is different from a bond, A can also be —CN.

The present invention also relates to the compounds of formula (I), wherein, when Y is different from a bond, A is halogen (Cl, Br or I), as intermediates products.

Examples of $C_1$–$C_3$—, $C_1$–$C_4$- or $C_1$–$C_6$-alkyl groups are methyl, ethyl, n-propyl, isopropyl, n-butyl, t-butyl, n-pentyl, n-hexyl.

Examples of 5- or 6-membered heterocyclic groups with 1–3 nitrogen atoms, which can optionally be substituted with 1–2 amino groups, are: 2-pyridyl, (3-hydroxy-2-pyridinyl)methyl, [2,6-bis(diethylamino)-4-pyrimidinyl], [2,6-bis-(allylamino)-4-pyrimidinyl], [2,6-bis(amino)-4-pyrimidinyl], [2,6-bis(pyrrolidin-1-yl)-4-pyrimidinyl], [2,6-bis(diethylamino)-5-benzoyl-4-pyrimidinyl], [2,6-bis(diethylamino)-5-acetyl-4-pyrimidinyl], [2,6-bis(pyrrolidin-1-yl)-5-acetyl-4-pyrimidinyl], [2,6-bis(pyrrolidin-1-yl)-5-benzoyl-4-pyrimidinyl], [4,6-bis(2-allylamino)-1,3,5-triazin-2-yl], [4,6-bis(2-propylamino)-1,3,5-triazin-2-yl], [4,6-bis(diethylamino)-1,3,5-triazin-2-yl], [4,6-bis(pyrrolidin-1-yl)-1,3,5-triazin-2-yl], [3,6-bis(diethylamino)-pyridin-2-yl], [3,6-bis(pyrrolidin-1-yl)-pyridin-2-yl], [3,6-bis(allylamino)-pyridin-2-yl], [3,6-bis(propargylamino)-pyridin-2-yl], [3,6-bis(N-ethyl-N-allylamino)-pyridin-2-yl].

Examples of mono-$C_1$–$C_6$-alkylamino groups are methylamino, ethylamino, propylamino, isopropylamino, n-butylamino, t-butylamino.

Examples of mono $C_3$–$C_6$-monoalkenyl- or monoalkinylamino groups are allylamino, propargylamino.

Examples of di-$C_1$–$C_6$-alkylamino groups are dimethylamino, diethylamino, methylethylamino, methylpropylamino, methylisopropylamino, diisopropylamino, methyl n-butylamino.

Examples of ($C_1$–$C_6$)-alkyl-($C_3$–$C_7$)alkenylamino groups are methylallylamino, ethylallylamino, propylallylamino, isopropylallylamino.

Examples of optionally substituted benzhydryl groups are: bis (p-fluorophenyl)-methyl; bis(p-chlorophenyl)-methyl. Examples of optionally substituted phenyl groups are: p-fluorophenyl; p-chlorophenyl.

When Y is a —(CRaRb)— group, Ra is preferably the same as Rb and they are methyl or, taken together with the carbon atom which they are linked to,. -are cyclopropyl, cyclopentyl or cyclohexyl.

When A is an ester group, it is preferably methoxycarbonyl, ethoxycarbonyl or tert-butoxycarbonyl.

When A is a —CO—NRcRd or —NRcRd group, Rc is preferably hydrogen and Rd is preferably pyridin-2-yl or Rc and Rd, taken together with the nitrogen atom, are a 4-thiomorpholino or 4,5-dithiaazepino group.

Particularly preferred compounds (I) are those in which B is a —CO—, —$CH_2$—O—CO—, —$CH_2$NHCO— or —$CH_2$—NHCS— group; D is an heterocycle selected from the group consisting of [2,6-bis(pyrrolidin-1-yl)-4-pyrimidinyl], [4,6-bis(pyrrolidin-1-yl)-1,3,5-triazin-2-yl] and [3,6-bis(diethylamino)-pyridin-2-yl]; Y is —(CRaRb)—, wherein Ra, which is the same as Rb, is hydrogen or methyl or, taken together, they are cyclopentyl or cyclohexyl; A is an ethoxycarbonyl, methane- or tolyl-sulfonamidocarbonyl, pyridin-2-yl-aminocarbonyl, N-methyl-hydroxylaminocarbonyl, N-(4,5-dithiaazepino)carbonyl, N-(4,5-dithiaazepino), 1-oxoethane, 1-oxopropane group.

Most preferred groups are those in which X is carbon, the other meanings being as defined above.

When in compounds of formula (I) an acid or basic group is present, it can be salified respectively with pharmaceutically acceptable bases or acids. The obtained non toxic salts, as well as the single enantiomers, diastereoisomers, diastereoisomeric mixtures and racemates of compounds (I) fall within the scope of the invention. The basic group can be salified with both inorganic and organic pharmaceutically acceptable acids, such as hydrochloric, hydrobromic, hydroiodic, phosphoric, metaphosphoric, nitric or sulfuric acids, acetic, oxalic, tartaric, citric, benzoic, glycolic, gluconic, glucuronic, succinic, maleic, fumaric acids and the like.

The carboxy group can be salified with bases of various nature, as long as they are pharmaceutically acceptable. Examples of said salts include those with: ammonium, sodium, potassium, calcium, magnesium, aluminium, iron, zinc, copper, argynine, lysine, histidine, methylamine, ethylamine, dimethylamine, dibenzylamine, morpholine, phenylglycine and D-glucosamine.

Prolinamides with piperazinequinazoline are described as ACE-inhibitors (Sankyo Co., JP 82 91,987; C.A., 97:198218w, 1982).

N-Carbamoylprolinamides with N-methylpiperazine are known as filaricides (Indian J. Chem., Sect. B, 1987, 26B(8), 748–751).

The compounds of the invention are effective in the prevention and/or reduction of respiratory tract hyper-reactivity and in resolving the phlogistic condition which accompanies acute and sub-chronical inflammations of bronchial mucosa.

Bronchial hyper-reactivity, which is a forewarner clinical symptom of asthmatic pathology, is considered to be a direct consequence of an abnormal and latent contractility and sensitivity of bronchial mucosa which can cause acute crisis of asthma in specific subjects, after physical exercise and/or exposure to outside stimuli, such as inhalation of fogs, pollutants, allergens and autacoids.

Most of the typical phenomenology of-the bronchial hyper-reactivity conditions can be simulated by an experimental model consisting in the forced inspiration of tobacco smoke (for example for 10 min.) in male guinea pigs weighing 400–450 g, in artificial respiration under ethyl urethane and pancuronium bromide anaesthesia (L. Gallico et al., American Review of Respiratory Disease, 141(4) Suppl., A840 (1990)).

The activity of the compounds of the invention, in the considered pharmacological model, is proved by the normalization of parameters resulting changed after forced inspiration of tobacco smoke, such as: persistent increase in the pulmonary inspiratory pressure (measured according to the technique of Konzett and Rossler, Naun. Schmied. Arch. Exper. Pathol. Pharmacol: 191, 71, 1970); increased cell count (leukocytes, eosinophils, epithelial cells) in bronchoalveolar lavage fluids (BAL); transudation into the bronchial tissue (trachea) of Evans Blue previously administered by the intravenous route.

The compounds of the invention, administered two hours before exposure to tobacco smoke, in dosages varying from 2 to 50 mg/kg, show a protective action which lasts at least 4–6 hours, and results in a reduction in the pressory increases induced by smoke inspiration, with a simultaneous normalization of cell count in BAL and an inhibition in dye transudation. Said pharmacological effects are dose-related and they appear after both oral and intramuscular administrations.

The compounds of the invention are effective also in inhibiting cough induced by exposure to a citric acid aerosol, in a dosage range varying from 30 to 60 mg/kg (Charlier R., et al. Arch. Int. Pharmacodyn. 134, 306–27, 1961).

What stated above clearly shows that the compounds of the invention can be used in human therapy for the treatment of asthma and obstructive conditions of the respiratory tract and in the cure and treatment of inflammatory phlogosis. For the envisaged therapeutical uses, the compounds of the invention will be administered in form of pharmaceutical compositions, which can be prepared with conventional excipients and techniques, such as those described in Remington's Pharmaceutical Sciences Handbook, Mack Pub. Co., New York, USA, 17th edition, 1985, suited for the intramuscular, intravenous, oral, aerosol and rectal administrations.

The daily dosage will depend on a number of factors, such as the severity of the disease and the conditions of the patient; generally such dosage will range from 1 to 50 mg of a compound of formula (I) for a patient weighing 70 kg, one or more times daily.

The compounds of formula (I) are prepared by reacting a compound of formula (II)

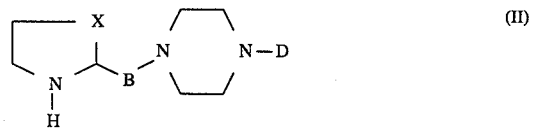

wherein X, B and D are as defined above, with a compound of formula (III)

wherein Y has the above mentioned meanings, A' has the same meanings as A with the exception of a free carboxy group or, when Y is different from a bond, it also can be halogen (Cl, Br or I) and E is halogen (Cl, Br), N-imidazolyl, OH, O-hydroxysuccinimidyl or, taken together with the carbonyl group, it forms a mixed anhydride with a carboxylic or sulfonic acid (for example trifluoromethanesulfonic acid), to give compounds of formula (Ia)

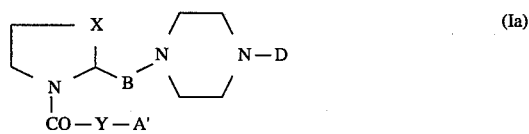

which, when A' is an ester group, can be transformed into compounds of formula (I) in which A is a free or esterified carboxy group, by hydrolysis with mineral bases such as alkali hydroxides, at various concentrations; the obtained acids can subsequently be resolved by salification with optically active bases and/or they can be transformed into the corresponding amides or esters of formula (I). On the contrary, in case A' is halogen (Cl, Br or I), compounds of formula (Ia) can be transformed into compounds of formula (I) in which A is

(with Rc and Rd as defined above), by reaction with the corresponding amines of formula

The reaction of compound (II) with compound (III) is generally performed in an inert solvent and in the presence of a suitable base. In case E—CO— is a carboxy group (E=OH), the reaction is carried out in an inert solvent and in the presence of condensing agents, such as carbodiimides, isonitriles, and the like.

Compounds of formula (II) are prepared starting from an acid of formula (IIa)

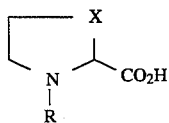
(IIa)

wherein R is a convenient protecting group, which can be removed without affecting the subsequent reactions neither the functional groups present in the molecule. Convenient protecting groups are: tert-butoxycarbonyl, methoxycarbonyl, 9-fluorenoxycarbonyl, 2,2,2-trichloroethoxycarbonyl, allyloxycarbonyl, benzyloxycarbonyl. Compounds of formula (IIa) can be subjected to salification and/or separation of the optical isomers as salts or diastereoisomeric compounds according to conventional methods.

Transformation of compounds of formula (IIa) into those of formula (IIb)

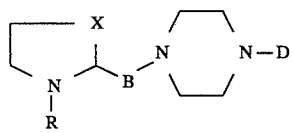
(IIb)

wherein R has the above mentioned meanings, can take place by means of conventional reactions, such as:

a) transformation of the carboxy group into succinimido ester, acid chloride, mixed anhydride or other known reactive derivatives thereof and subsequent condensation with an amine of formula (IIc)

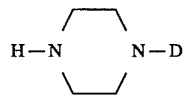
(IIc)

b) reduction of the carboxy group or of the corresponding mixed anhydride or of a carboxyester group deriving therefrom to primary alcohol (CH$_2$OH) which, after transformation into the corresponding halide or sulfonate, can be converted into an alkylamine by reaction with an amine of formula (IIc); suitable reducing agents include diborane or a borohydride of an alkali or alkaline-earth metal;

c) alcohols obtained according to b) can be converted into the corresponding azides by the Mitsunobu reaction with hydrazoic acid or, after transformation into the corresponding halide or sulfonate, by reaction with the azide of an alkali metal. The above alkylazides can then be transformed into amines by reduction, for example with trialkyl- or triaryl-phosphines, trialkyl phosphites, metal hydrides, alkaline-earth metals and the like;

d) halides or sulfonates obtained according to b) can be converted into the corresponding amines by means of conventional reactions, such as Gabriel synthesis or a reaction with amino group precursors, such as hexamethylenetetramine or trifluoroacetamide which can give the desired amine, by hydrolysis under appropriate conditions;

e) alcohols obtained according to b) and amines obtained according to c) can respectively be converted into carbamates, thiocarbamates, ureas or thioureas, by reaction with carbonyldiimidazole or thiocarbonyldiimidazole and subsequently with an amine of formula (IIc).

Transformation of compounds of formula (IIb) into compounds of formula (II) can be performed according to conventional methods for the specific and selective removal of the used protecting group, particularly, in case of BOC-derivatives, using trifluoroacetic acid or trimethylsilyl iodide.

Compounds of formula (III) can be prepared starting from compounds of formula (IIIa)

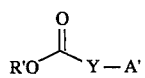
(IIIa)

wherein R' is (C$_1$–C$_2$) alkyl, Y and A' are as defined above, according to conventional methods which are reported in literature. Compounds of formula (IIIa), in their turn, are obtained following conventional procedures which are disclosed in literature.

Compounds of formula (I) of the invention can also be prepared by reacting a precursor of formula (IId)

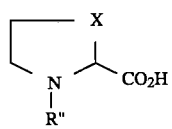
(IId)

wherein R" is —CO—Y—A', Y and A' being as defined above, with an amine of formula (IIc)

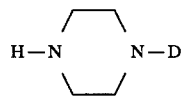
(IIc)

Said synthesis can be performed by means of conventional reactions, such as those reported in items a), b), c), d) and e) for the transformation of compounds of formula (IIa) into those of formula (IIb). Particularly, separation of the optical isomers can be obtained by salificating racemic mixtures of compounds of formula (IId) with optically active amines, such as (−) or (+)-quinine, separating the resulting diastereoisomeric salt by crystallization, recrystallizing to constant [α]$_D$ and finally obtaining the free acid and recovering the resolution agent.

Amines of formula (IIc) are prepared according to the processes described in PCT WO 87/01706.

In the following Examples, concentrations are expressed as % w/v, if not otherwise stated. The described compounds must be considered as racemic mixtures, if not otherwise specified by means of (+) and (−).

EXAMPLE 1

A solution of 26.5 g of (1-ethoxymalonyl)-1,3-thiazolidine-2-carboxylic acid (0.107 mole) and 34.8 g of (−)-quinine (0.107 mole) in acetonitrile (2.5 l) is filtered and stirred for 36 hours at room temperature. A white precipitate is obtained (24.1 g), m.p. 156°–157° C., which is recrystallized from acetonitrile (560 ml), to give 21 g of (−)-quinine (+)-thiazolidinecarboxylate, m.p. 170°–172° C., [α]$_D$=−43°, [α]$_{546}$=−53.5° with c=2.3 in chloroform.

Mother liquors from the first crystallization are concentrated to dryness and water is distilled as an azeotrope with methanol and acetone (50 ml). The solid residue is suspended in acetone (400 ml), refluxed for 30 min., then cooled to room temperature. After two hour stirring, the suspended solid is filtered (21 g, m.p. 156°–158° C., $[\alpha]_D=$ –124°, $[\alpha]_{546}=$–151° with c=2.3 in chloroform). The crystalline solid is suspended again in acetone (200 ml) and refluxed for 30 min., to obtain 12.1 g of (–)-quinine, m.p. 164°–166° C., $[\alpha]_D=$–143°, $[\alpha]_{546}=$–174° with c=1.9 in chloroform.

By displacement of the optically active base with 2N sulfuric acid and extraction with ethyl acetate (3×100 ml) the optically active acids are recovered in form of oils: (+)-(1-ethoxymalonyl)-1,3-thiazolidine-2-carboxylic acid, $[\alpha]_D=+$ 33°, $[\alpha]_{546}=+37°$ with c=2.7 in chloroform; (–)-(1-ethoxymalonyl)-1,3-thiazolidine-2-carboxylic acid $[\alpha]_D=$–32°, $[\alpha]_{546}=$–35° with c=2.2 in chloroform.

EXAMPLE 2

A solution containing 2.5 g of BOC-L-proline in anhydrous THF (10 ml), at a temperature of 0° C., under inert gas atmosphere and with stirring, is added with 2.9 g of N-hydroxysuccinimide dissolved in 10 ml of tetrahydrofuran (THF). A solution of 2.1 ml of morpholinoethylisonitrile in 5 ml of THF is dropped into the resulting solution and stirring is continued for 2 hours at room temperature; then the solution is acidified with 1N hydrochloric acid (litmus paper) and extracted with ethyl acetate (3×10 ml). The combined organic extracts are concentrated under vacuum until BOC-L-proline succinimido ester crystallizes, which is recovered by filtration to obtain 2.6 g, m.p. 128°–130° C.

1 g of BOC-L-proline succinimido ester is dissolved at room temperature, under inert gas atmosphere, in acetonitrile (7 ml), then, under stirring, it is added with 0.97 g of N-[4,6 -bis(pyrrolidin-1-yl) -1,3,5-triazin-2-yl]piperazine dissolved in acetonitrile (5 ml). After 5 hours, the mixture is concentrated under vacuum to small volume, then it is added with a sodium bicarbonate saturated solution to slightly basic pH. The solution is extracted with ethyl acetate (3×10 ml), then the combined extracts are concentrated to small volume under vacuum. By addition of ethyl ether, 1.5 g of N-[(pyrrolidin-1-tert-butoxycarbonyl-2-yl)carbonyl]-N'-[4, 6-bis(pyrrolidin-1-yl)-1,3,5-triazin-2-yl]piperazine precipitates, m.p. 148° C. (after recrystallization from diisopropyl ether), $[\alpha]_D=$–20.25° (c=2.01 in EtOH).

EXAMPLE 3

By reacting an acetonitrile solution of BOC-proline N-hydroxysuccinimido ester with an appropriate N-substituted piperazine, according to the procedure described in Example 2, the following N,N'-disubstituted piperazines are obtained:

N'-[(pyrrolidin-1-tert-butoxycarbonyl-2-yl)carbonyl]-N-(pyridin- 2-yl)piperazine, N'-[(pyrrolidin-1-tert-butoxycarbonyl-2-yl)carbonyl]-N-[2, 6-bis(diethylamino)pyrimidin-4-yl]piperazine, N'-[(pyrrolidin-1-tert-butoxycarbonyl-2-yl)carbonyl]-N-[2, 6-bis(allylamino)pyrimidin-4-yl]piperazine, (–)-N'-[(pyrrolidin-1-tert-butoxycarbonyl-2-yl)carbonyl] -N-[2,6-bis(pyrrolidin-1-yl)pyrimidinil-4-yl]piperazine, m.p. 168°–170° C., $[\alpha]_D=$–20.7° (c=2 in EtOH), (+)-N'-[(pyrrolidin-1-tert-butoxycarbonyl-2-yl)carbonyl] -N-[2,6-bis(pyrrolidin-1-yl)pyrimidin-4 -yl]piperazine, $[\alpha]_D=+20.2°$ (c=2.03 in EtOH), N'-[(pyrrolidin-1-tert-butoxycarbonyl-2-yl)carbonyl]-N-[2, 6-bis(pyrrolidin-1-yl)pyrimidin-4-yl]piperazine, m.p. 125° C., N'-[(pyrrolidin-1-tert-butoxycarbonyl-2-yl)carbonyl]-N-[ 2,6-bis(diamino)pyrimidin-4-yl]piperazine, N'-[(pyrrolidin-1-tert-butoxycarbonyl-2-yl)carbonyl]-N-[2, 6-bis(diethylamino)-5-benzoylpyrimidin-4-yl]piperazine, N'-[(pyrrolidin-1-tert-butoxycarbonyl-2-yl)carbonyl]-N-[2, 6-bis(diethylamino)-5-acetylpyrimidin-4-yl]piperazine, N'-[(pyrrolidin-1-tert-butoxycarbonyl-2-yl)carbonyl]-N-[2, 6-bis(pyrrolidin-1-yl)-5-acetylpyrimidin-4-yl]piperazine, N'-[(pyrrolidin-1-tert-butoxycarbonyl-2-yl)carbonyl]-N-[2, 6-bis(pyrrolidin-1-yl)-5-benzoylpyrimidin-4-yl]piperazine, N'-[(pyrrolidin-1-tert-butoxycarbonyl-2-yl)carbonyl]-N-[4, 6-bis(allylamino)-1,3,5-triazin-2-yl]piperazine, N'-[(pyrrolidin-1-tert-butoxycarbonyl-2-yl)carbonyl]-N-[4, 6-bis(2-propylamino)-1,3,5-triazin-2-yl]piperazine, N'-[(pyrrolidin-1-tert-butoxycarbonyl-2-yl)carbonyl]-N-[4, 6-bis(diethylamino)-1,3,5-triazin-2-yl]piperazine, (–)-N'-[(pyrrolidin-1-tert-butoxycarbonyl-2-yl)carbonyl] -N-[3,6-bis(diethylamino)pyridin-2-yl]piperazine, $[\alpha]_D=$ –19.3° (c=2.07 in EtOH), (+)-N'-[(pyrrolidin-1-tert-butoxycarbonyl-2-yl)carbonyl] -N-[3,6-bis(diethylamino)pyridin-2-yl]piperazine, $[\alpha]_D=$ +19.8° (c=2.01 in EtOH), N'-[(pyrrolidin-1-tert-butoxycarbonyl-2-yl)carbonyl]-N-[3, 6-bis(pyrrolidin-1-yl)pyridin-2-yl]piperazine, N'-[(pyrrolidin-1-tert-butoxycarbonyl-2-yl)carbonyl]-N-[3, 6-bis(allylamino)pyridin-2-yl]piperazine, N'-[(pyrrolidin-1-tert-butoxycarbonyl-2-yl)carbonyl]-N-[3, 6-bis(propargylamino)pyridin-2-yl]piperazine, N'-[(pyrrolidin-1-tert-butoxycarbonyl-2-yl)carbonyl]-N-[3, 6-bis(N-ethyl-N-allylamino)pyridin-2-yl]piperazine, N'-[(pyrrolidin-1-tert-butoxycarbonyl-2-yl)carbonyl] -N((3-hydroxy-2-pyridinyl)methyl)piperazine.

EXAMPLE 4

2.54 ml of trifluoroacetic acid are added, with stirring and under inert gas atmosphere, to a solution of 1.4 g of N-[(pyrrolidin-1-tert-butoxycarbonyl-2-yl] carbonyl]-N'-[4, 6-bis(pyrrolidin-1-yl)-1,3,5-triazin- 2-yl]piperazine in 10 ml of methylene chloride. After 3 hours at room temperature, the reaction mixture is added with 1N NaOH to basic pH, then it is extracted with methylene chloride and repeatedly washed with water.

The organic extracts are dried over sodium sulfate and solvent is evaporated off under reduced pressure. The crude product is crystallized from ethyl ether, to obtain 950 mg of N-[(pyrrolidin-2-yl)carbonyl]-N'-[4,6 -bis(pyrrolidin-1-yl)-1,3,5-triazin-2-yl]piperazine, m.p. 143° C., $[\alpha]_D=$–65.75° (c=0,23 in EtOH).

EXAMPLE 5

By reacting the N,N'-disubstituted piperazines described in Example 3, according to the procedure described in Example 4, the following N'-substituted N-[(pyrrolidin-2-yl)carbonyl]piperazines are obtained:

N'-[(pyrrolidin-2-yl)carbonyl]-N-(pyridin-2-yl)piperazine,

N'-[(pyrrolidin-2-yl)carbonyl]-N-[2,6-bis(diethylamino)pyrimidin- 4-yl]piperazine, N'-[(pyrrolidin-2-yl)carbonyl]-N-[2,6-bis(allylamino)pyrimidin- 4-yl]piperazine, (−)-N'-[(pyrrolidin-2-yl)carbonyl]-N-[2,6-bis(pyrrolidin-1-yl)pyrimidin-4-yl]piperazine, m.p. 172°–174° C., $[\alpha]_D=-56.6°$ (c=1.88 in EtOH), (+)-N'-[(pyrrolidin-2-yl)carbonyl]-N-[2,6-bis(pyrrolidin-1-yl)pyrimidin-4-yl]piperazine, m.p. 148°–151° C., $[\alpha]_D=+53.5°$ (c=2.02 in EtOH), N'-[(pyrrolidin-2-yl)carbonyl]-N-[2,6-bis(pyrrolidin-1-yl)pyrimidin-4-yl]piperazine, m.p. 137° C., N'-[(pyrrolidin-2-yl)carbonyl]-N-[2,6-bis(diamino)pyrimidin-4-yl]piperazine, N'-[(pyrrolidin-2-yl)carbonyl]-N-[2,6-bis(diethylamino)-5-benzoylpyrimidin-4-yl]piperazine, N'-[(pyrrolidin-2-yl)carbonyl]-N-[2,6-bis(diethylamino)-5-acetylpyrimidin-4-yl]piperazine, N'-[(pyrrolidin-2-yl)carbonyl]-N-[2,6-bis(pyrrolidin-1-yl)-5-acetylpyrimidin-4-yl]piperazine, N -[(pyrrolidin-2-yl)carbonyl]-N-[2,6-bis(pyrrolidin-1-yl)-5-benzoylpyrimidin-4-yl]piperazine, N'-[(pyrrolidin-2-yl)carbonyl]-N-[4,6-bis(allylamino)-1,3,5-triazin-2-yl]piperazine, N'-[(pyrrolidin-2-yl)carbonyl]-N-[4,6-bis(2-propylamino)-1,3,5-triazin-2-yl]piperazine, N'-[(pyrrolidin-2-yl)carbonyl]-N-[4,6-bis(diethylamino)-1,3,5-triazin-2-yl]piperazine, (−)-N'-[(pyrrolidin-2-yl)carbonyl]-N-[3,6-bis(diethylamino)pyridin-2-yl]piperazine, oil, $[\alpha]_D=-43.3°$ (c=2.56 in EtOH), (+)-N'-[(pyrrolidin-2-yl)carbonyl]-N-[3,6-bis(diethylamino)pyridin-2-yl]piperazine, $[\alpha]_D=+48.4°$ (c=2.01 in EtOH), N'-[(pyrrolidin-2-yl)carbonyl]-N-[3,6-bis(pyrrolidin-1-yl)pyridin-2-yl]piperazine, N'-[(pyrrolidin-2-yl)carbonyl]-N-[3,6-bis(allylamino)pyridin-2-yl]piperazine, N'-[(pyrrolidin-2-yl)carbonyl]-N-[3,6-bis(propargylamino)pyridin-2-yl]piperazine, N'-[(pyrrolidin-2-yl)carbonyl]-N-[3,6-bis(N-ethyl-N-allylamino)pyridin-2-yl]piperazine, N'-[(pyrrolidin-2-yl)carbonyl]-N-((3-hydroxy-2-pyridinyl)methyl)piperazine.

EXAMPLE 6

0.8 g of N-[(pyrrolidin-2-yl)carbonyl]-N'-[4,6-bis(pyrrolidin-1-yl)-1,3,5-triazin-2-yl]piperazine dissolved in 20 ml of acetonitrile are added at 0° C. and under stirring, with 0.22 g of potassium bicarbonate and with a solution of 0.28 ml of ethyl malonyl chloride in 5 ml of acetonitrile. After 4 hours at room temperature and under stirring, the reaction mixture is added with water (50 ml) and extracted repeatedly with ethyl acetate (3×20 ml). The organic extracts are dried over sodium sulfate and solvent is evaporated off under reduced pressure. The residue (0.86 g) is purified by silica gel chromatography (eluent 1:1 hexane/AcOEt), to give N-[(1-ethoxymalonylpyrrolidin-2-yl)carbonyl]-N'-[4,6-bis(pyrrolidin-1-yl)-1,3,5-triazin-2-yl]piperazine, m.p. 95° C., $[\alpha]_D=-23.95°$ (c=0.2 in EtOH).

EXAMPLE 7

According to the procedure described in Example 6, starting from the N,N'-disubstituted piperazines described in Example 5 and from optionally 2-substituted malonic acid monoester-monochlorides, and from cyanoacetil chloride, the following piperazines are prepared:

N'-[(1-ethoxymalonylpyrrolidin-2-yl)carbonyl]-N-(pyridin-2-yl)piperazine,

N'-[(1-ethoxymalonylpyrrolidin-2-yl)carbonyl]-N-[2,6-bis(diethylamino)pyrimidin-4-yl]piperazine, N'-[(1-ethoxymalonylpyrrolidin-2-yl)carbonyl]-N-[2,6-bis(allylamino)pyrimidin-4-yl]piperazine, (−)-N'-[(1-ethoxymalonylpyrrolidin-2-yl)carbonyl]-N-[2,6-bis(pyrrolidin-1-yl)pyrimidin-4-yl]piperazine, m.p. 170°–172° C., $[\alpha]_D=-26.5$ (c=2.19 in EtOH), (+)-N'-[(1-ethoxymalonylpyrrolidin-2-yl)carbonyl]-N-[2,6-bis(pyrrolidin-1-yl)pyrimidin-4-yl]piperazine, m.p. 133–135° C., $[\alpha]_D=+26.5°$ (c=2.14 in EtOH)

N'-[(1-ethoxymalonylpyrrolidin-2-yl)carbonyl]-N-[2,6-bis(pyrrolidin-1-yl)pyrimidin-4-yl]piperazine, m.p. 127°–129° C., N'-[(1-ethoxymalonylpyrrolidin-2-yl)carbonyl]-N-[2,6-bis(diamino)-pyrimidin-4-yl]piperazine, N'-[(1-ethoxymalonylpyrrolidin-2-yl)carbonyl]-N-[2,6-bis(diethylamino)-5-benzoylpyrimidin-4-yl]piperazine, N'-[(1-ethoxymalonylpyrrolidin-2-yl)carbonyl]-N-[2,6-bis(diethylamino)-5-acetylpyrimidin-4-yl]piperazine, N'-[(1-ethoxymalonylpyrrolidin-2-yl)carbonyl]-N-[2,6-bis(pyrrolidin-1-yl)-5-acetylpyrimidin-4-yl]piperazine, N'-[(1-ethoxymalonylpyrrolidin-2-yl)carbonyl]-N-[2,6-bis(pyrrolidin-1-yl)-5-benzoylpyrimidin-4-yl]piperazine, N'-[(1-ethoxymalonylpyrrolidin-2-yl)carbonyl]-N-[4,6-bis(allylamino)-1,3,5-triazin-2-yl]piperazine, N'-[(1-ethoxymalonylpyrrolidin-2-yl)carbonyl]-N-[4,6-bis(2-propylamino)-1,3,5-triazin-2-yl]piperazine, N'-[(1-ethoxymalonylpyrrolidin-2-yl)carbonyl]-N-[4,6-bis(diethylamino)-1,3,5-triazin-2-yl]piperazine, (−)-N'-[(1-ethoxymalonylpyrrolidin-2-yl)carbonyl]-N-[3,6-bis(diethylamino)pyridin-2-yl]piperazine, m.p. of hydrochloride 80°–85° C., $[\alpha]_D=-20.6°$ (free base, c=2.09 in EtOH), (+)-N'-[(1-ethoxymalonylpyrrolidin-2-yl)carbonyl]-N-[3,6-bis(diethylamino)pyridin-2-yl]piperazine, $[\alpha_D=+20.1°$ (c=2.01 in EtOH), N'-[(1-ethoxymalonylpyrrolidin-2-yl)carbonyl]-N-[3,6-bis(pyrrolidin-1-yl)pyridin-2-yl]piperazine, N'-[(1-ethoxymalonylpyrrolidin-2-yl)carbonyl]-N-[3,6-bis(allylamino)pyridin-2-yl]piperazine, N'-[(1-ethoxymalonylpyrrolidin-2-yl)carbonyl]-N-[3,6-bis(propargylamino)pyridin-2-yl]piperazine, N'-[(1-ethoxymalonylpyrrolidin-2-yl)carbonyl]-N-[3,6-bis(N-ethyl-N-allylamino)pyridin-2-yl]piperazine, N'-[(1-ethoxymalonylpyrrolidin-2-yl)carbonyl]-N-[3-hydroxy-2-pyridinylmethyl)piperazine, N'-[(1-((2',2'-dimethyl)ethoxymalonyl)pyrrolidin-2-yl)carbonyl]-N-(pyridin-2-yl)piperazine, N'-[(1-((2',2'-dimethyl)ethoxymalonyl)pyrrolidin-2-yl)carbonyl]-N-(2,6-bis(diethylamino)pyrimidin-4-yl]piperazine, N'-[(1-((2',2'-dimethyl)ethoxymalonyl)pyrrolidin-2-yl)carbonyl]-N-(2,6-bis(allylamino)pyrimidin-4-yl]piperazine, (−)-N'-[(1-((2',2'-dimethyl)ethoxymalonyl)pyrrolidin-2-yl)carbonyl]-N-[2,6-bis(pyrrolidin-1-yl)pyrimidin-4-yl]piperazine, m.p. 139°–140° C., $[\alpha]_D=-15.3°$ (c=0.2 in EtOH), N'-[(1-((2',2'-dimethyl)ethoxymalonyl)pyrrolidin-2-yl)-carbonyl]-N-[2,6-bis(diamino)pyrimidin-4-yl]piperazine, N'-[(1-((2',2'-dimethyl)ethoxymalonyl)pyrrolidin-2-yl)carbonyl]-N-[2,6-bis(diethylamino)-5-benzoylpyrimidin-4-yl]piperazine, N'-[(1-((2',2'-dimethyl)ethoxymalonyl)pyrrolidin-2-yl)carbonyl]-N-[2,6-bis(diethylamino)-5-acetylpyrimidin-4-yl]piperazine, N'-[(1-((2',2'-dimethyl)ethoxymalonyl)pyrrolidin-2-yl)carbonyl]-N-[2,6-bis(pyrrolidin-1-yl)-5-acetylpyrimidin-4-yl]piperazine, N'-[(1-((2',2'-dimethyl)ethoxymalonyl)pyrrolidin-2-yl)carbonyl]-N-[2,6-bis(pyrrolidin-1-yl)-5-benzoylpyrimidin-4-yl]piperazine, N'-[(1-((2',2'-dimethyl)ethoxymalonyl)pyrrolidin-2-yl)carbonyl]-N-[4,6-bis(allylamino)-1,3,5-triazin-2-yl]piperazine, N'-[(1-((2',2'-dimethyl)ethoxymalonyl)pyrrolidin-2-yl)carbonyl]-N-[4,6-bis(pyrrolidin-1-yl)-1,3,5-triazin-2-yl]piperazine, N'-[(1-((2',2'-dimethyl)ethoxymalonyl)pyrrolidin-2-yl)carbonyl]-N-[4,6-bis(2-propylamino)-1,3,5-triazin-2 -yl]piperazine, N'-[(1-((2',2'-dimethyl)ethoxymalonyl)pyrrolidin-2-yl)carbonyl]-N-[4,6-bis(diethylamino)-1,3,5-triazin-2-yl]piperazine, N'-[(1-((2',2'-dimethyl)ethoxymalonyl)pyrrolidin-2-yl)carbonyl]-N-[3,6-bis(diethylamino)pyridin-2-yl]piperazine, N'-[(1-((2',2'-dimethyl)ethoxymalonyl)pyrrolidin-2-yl)carbonyl]-N-[3,6-bis(pyrrolidin-1-yl)pyridin-2-yl]piperazine, N'-[(1-((2',2'-dimethyl)ethoxymalonyl)pyrrolidin-2-yl)carbonyl]-N-[3,6-bis(allylamino)pyridin-2-yl]piperazine, N'-[(1-((2',2'-dimethyl)ethoxymalonyl)pyrrolidin-2-yl)carbonyl]-N-[3,6-bis(propargylamino) pyridin-2-yl]piperazine, N'-[(1-((2',2'-dimethyl)ethoxymalonyl)pyrrolidin-2-yl)carbonyl]-N-[3,6-bis(N-ethyl-N-allylamino)pyridin-2-yl]piperazine, N'-[(1-((2',2'-dimethyl)ethoxymalonyl)pyrrolidin-2-yl)carbonyl]-N-(3-hydroxy-2-pyridinylmethyl)piperazine, N'-[(1-(1'-(ethoxycarbonyl)cyclopentane-1'-carbonyl)pyrrolidin-2-yl)carbonyl]-N-(pyridin-2-yl)piperazine, N'-[(1-(1'-(ethoxycarbonyl)cyclopentane-1'-carbonyl)pyrrolidin-2-yl)carbonyl]-N-[2,6-bis(diethylamino)pyrimidin-4-yl]piperazine, N'-[(1-(1'-(ethoxycarbonyl)cyclopentane-1'-carbonyl)pyrrolidin-2-yl)carbonyl]-N-[2,6-bis(allylamino)pyrimidin-4-yl]piperazine, (–)-N'-[(1-(1'-(ethoxycarbonyl)cyclopentane-1'-carbonyl)pyrrolidin-2-yl)carbonyl]-N-[2,6-bis(pyrrolidin-1-yl)pyrimidin-4-yl]piperazine, hydrochloride m.p. 189°–90° C., N'-[(1-(1'-(ethoxycarbonyl)cyclopentane-1'-carbonyl)pyrrolidin-2-yl)carbonyl]-N-[2,6-bis(diamino)pyrimidin-4-yl]piperazine, N'-[(1-(1'-(ethoxycarbonyl)cyclopentane-1'-carbonyl)pyrrolidin-2-yl)carbonyl]-N-[2,6-bis(diethylamino)-5-benzoylpyrimidin-4-yl]piperazine, N'-[(1-(1'-(ethoxycarbonyl)cyclopentane-1'-carbonyl)pyrrolidin-2-yl)carbonyl]-N-[2,6-bis(diethylamino)-5-acetylpyrimidin-4-yl]piperazine, N'-[(1-(1'-(ethoxycarbonyl)cyclopentane-1'-carbonyl)pyrrolidin-2-yl)carbonyl]-N-[2,6-bis(pyrrolidin-1-yl)-5-acetylpyrimidin-4-yl]piperazine, N'-[(1-(1'-(ethoxycarbonyl)cyclopentane-1'-carbonyl)pyrrolidin-2-yl)carbonyl]-N-[2,6-bis(pyrrolidin-1-yl)-5-benzoylpyrimidin-4-yl]piperazine, N'-[(1-(1'-(ethoxycarbonyl)cyclopentane-1'-carbonyl)pyrrolidin-2-yl)carbonyl]-N-[4,6-bis(allylamino)-1,3,5-triazin-2-yl]piperazine, N'-[(1-(1'-(ethoxycarbonyl)cyclopentane-1'-carbonyl)pyrrolidin-2-yl)carbonyl]-N-[4,6-bis(pyrrolidin-1-yl)-1,3,5-triazin-2-yl]piperazine, N'-[(1-(1'-(ethoxycarbonyl)cyclopentane-1'-carbonyl)pyrrolidin-2-yl)carbonyl]-N-[4,6-bis(2-propylamino)-1,3,5-triazin-2-yl]piperazine, N'-[(1-(1'-(ethoxycarbonyl)cyclopentane-1'-carbonyl)pyrrolidin-2-yl)carbonyl]-N-[4,6-bis(diethylamino)-1,3,5-triazin-2-yl]piperazine, N'-[(1-(1'-(ethoxycarbonyl)cyclopentane-1-carbonyl)pyrrolidin-2-yl)carbonyl]-N-[3,6-bis(diethylamino)pyridin-2-yl]piperazine, N'-[(1-(1'-(ethoxycarbonyl)cyclopentane-1-carbonyl)pyrrolidin-2-yl)carbonyl]-N-[3,6-bis(pyrrolidin-1-yl)pyridin-2-yl]piperazine, N'-[(1-(1'-(ethoxycarbonyl)cyclopentane-1-carbonyl)pyrrolidin-2-yl)carbonyl]-N-[3,6-bis(allylamino)pyridin-2-yl] piperazine, N'-[(1-(1'-(ethoxycarbonyl)cyclopentane-1-carbonyl)pyrrolidin-2-yl)carbonyl]-N-[3,6-bis(propargylamino)pyridin-2-yl]piperazine, N'-[(1-(1'-(ethoxycarbonyl)cyclopentane-1'-carbonyl)pyrrolidin-2-yl)carbonyl]-N-[3,6-bis(N-ethyl-N-allylamino)pyridin-2-yl]piperazine, N'-[(1-(1'-(ethoxycarbonyl)cyclopentane-1'-carbonyl)pyrrolidin-2-yl)carbonyl]-N-(3-hydroxy-2-pyridinilmethyl)piperazine, N'-[(1-(1'-(ethoxycarbonyl)cyclohexane-1'-carbonyl)pyrrolidin-2-yl)carbonyl]-N-(pyridin-2-yl)piperazine, N'-[(1-(1'-(ethoxycarbonyl)cyclohexane-1'-carbonyl)pyrrolidin-2-yl)carbonyl I-N-[2,6-bis(diethylamino)pyrimidin-4-yl]piperazine, N'-[(1-(1'-(ethoxycarbonyl)cyclohexane-1'-carbonyl)pyrrolidin-2-yl)carbonyl]-N-[2,6-bis(allylamino)pyrimidin-4-yl]piperazine, (–)-N'-[(1-(1'-(ethoxycarbonyl)cyclohexane-1'-carbonyl)pyrrolidin-2-yl)carbonyl]-N-[2,6-bis(pyrrolidin-1-yl)pyrimidin-4-yl]piperazine, m.p. 192°–193° C., $[\alpha]_D = -19.6°$ (c=0.2 in EtOH), N'-[(1-(1'-(ethoxycarbonyl)cyclohexane-1'-carbonyl)pyrrolidin-2-yl)carbonyl]-N-[2,6-bis(diamino)pyrimidin-4-yl] piperazine, N'-[(1-(1'-(ethoxycarbonyl)cyclohexane-1'-carbonyl)pyrrolidin-2-yl)carbonyl]-N-[2,6-bis(diethylamino)-5-benzoylpyrimidin-4-yl]piperazine, N'-[(1-(1'-(ethoxycarbonyl)cyclohexane-1'-carbonyl)pyrrolidin-2-yl)carbonyl]-N-[2,6-bis(diethylamino)-5-acetylpyrimidin-4-yl]piperazine, N'-[(1-(1'-(ethoxycarbonyl)cyclohexane-1'-carbonyl)pyrrolidin-2-yl)carbonyl]-N-[2,6-bis(pyrrolidin-1-yl)-5-acetylpyrimidin-4-yl]piperazine, N'-[(1-(1'-(ethoxycarbonyl)cyclohexane-1'-carbonyl)pyrrolidin-2-yl)carbonyl]-N-[2,6-bis(pyrrolidin-1-yl)-5-benzoylpyrimidin-4-yl]piperazine, N'-[(1-(1'-(ethoxycarbonyl)cyclohexane-1'-carbonyl)pyrrolidin-2-yl)carbonyl]-N-[4,6-bis(allylamino)-1,3,5-triazin-2-yl]piperazine, N'-[(1-(1'-(ethoxycarbonyl)cyclohexane-1'-carbonyl)pyrrolidin-2-yl)carbonyl]-N-[4,6-bis(pyrrolidin-1-yl)-1,3,5-triazin-2-yl]piperazine, N'-[(1-(1'-(ethoxycarbonyl)cyclohexane-1'-carbonyl)pyrrolidin-2-yl)carbonyl]-N-[4,6-bis(2-propylamino)-1,3,5-triazin-2-yl]piperazine, N'-[(1-(1'-(ethoxycarbonyl)cyclohexane-1'-carbonyl)pyrrolidin-2-yl)carbonyl]-N-[4,6-bis(diethylamino)-1, 3,5-triazin-2-yl]piperazine, N'-[(1-(1'-(ethoxycarbonyl)cyclohexane-1'-carbonyl)pyrrolidin-2-yl)carbonyl]-N-[3,6-bis(diethylamino)pyridin-2-yl]piperazine, N'-[(1-(1'-(ethoxycarbonyl)cyclohexane-1'-carbonyl)pyrrolidin-2-yl)carbonyl]-N-[3,6-bis(pyrrolidin-1-yl)pyridin-2-yl]piperazine, N'-[(1-(1'-(ethoxycarbonyl)cyclohexane-1'-carbonyl)pyrrolidin-2-yl)carbonyl]-N-[3,6-bis(allylamino)pyridin-2-yl] piperazine, N'-[(1-(1'-(ethoxycarbonyl)cyclobutane-1'-carbonyl)pyrrolidin-2-yl)carbonyl]-N-[3,6-bis(propargylamino)pyridin-2-yl]piperazine, N'-[(1-(1'-(ethoxycarbonyl)cyclopropane-1'-carbonyl)pyrrolidin-2-yl)carbonyl I-N-[3,6-bis(N-ethyl-N-allylamino)pyridin-2-yl]piperazine, N'-[(1-(1'-(ethoxycarbonyl)cyclohexane-1'-carbonyl)pyrrolidin-2-yl)carbonyl]-N-[3-hydroxy-2-pyridinylmethyl)piperazine, N'-[(1-(cyanomethylcarbonyl)pyrrolidin-2-yl)carbonyl]-N-(pyridin-2-yl)piperazine, N'-[(1-(cyanomethylcarbonyl)pyrrolidin-2-yl)carbonyl]-N-[2,6-bis(diethylamino)pyrimidin-4-yl]piperazine, N'-[(1-(cyanomethylcarbonyl)pyrrolidin-2-yl)carbonyl]-N-[2,6-bis(allylamino)pyrimidin-4-yl]piperazine, (−)-N'-[(1-(cyanomethylcarbonyl)pyrrolidin-2 -yl)carbonyl]-N-[2,6-bis(pyrrolidin-1-yl)pyrimidin-4-yl]piperazine, m.p. 198°–199° C., $[\alpha]_D = -8.4°$ (c=0.19 in DMF), N'-[(1-(cyanomethylcarbonyl)pyrrolidin-2-yl)carbonyl]-N-[2,6-bis(diethylamino)-5-benzoylpyrimidin-4-yl]piperazine, N'-[(1-(cyanomethylcarbonyl)pyrrolidin-2-yl)carbonyl]-N-[2,6-bis(diethylamino)-5-acetylpyrimidin-4-yl]piperazine, N'-[(1-(cyanomethylcarbonyl)pyrrolidin-2-yl)carbonyl]-N-[2,6-bis(pyrrolidin-1-yl)-5-acetylpyrimidin-4-yl]piperazine, N'-[(1-(cyanomethylcarbonyl)pyrrolidin-2-yl)carbonyl]-N-[2,6-bis(pyrrolidin-1-yl)-5-benzoylpyrimidin-4-yl]piperazine, N'-[(1-(cyanomethylcarbonyl)pyrrolidin-2-yl)carbonyl]-N-[4,6-bis(allylamino)-1,3,5-triazin-2-yl]piperazine, N'-[(1-(cyanomethylcarbonyl)pyrrolidin-2-yl)carbonyl]-N-[4,6-bis(pyrrolidin-1-yl)-1,3,5-triazin-2-yl]piperazine, N'-[(1-(cyanomethylcarbonyl)pyrrolidin-2-yl)carbonyl]-N-[4,6-bis(2-propylamino)-1,3,5-triazin-2-yl]piperazine, N'-[(1-(cyanomethylcarbonyl)pyrrolidin-2-yl)carbonyl]-N-[4,6-bis(diethylamino)-1,3,5-triazin-2-yl]piperazine, N'-[(1-(cyanomethylcarbonyl)pyrrolidin-2-yl)carbonyl]-N-[3,6-bis(diethylamino)pyridin-2-yl]piperazine, N'-[(1-(cyanomethylcarbonyl)pyrrolidin-2-yl)carbonyl]-N-[3,6-bis(pyrrolidin-1-yl)pyridin-2-yl]piperazine, N'-[(1-(cyanomethylcarbonyl)pyrrolidin-2-yl)carbonyl]-N-[3,6-bis(allylamino)pyridin-2-yl]piperazine, N'-[(1-(cyanomethylcarbonyl)pyrrolidin-2-yl)carbonyl]-N-[3,6-bis(propargylamino)pyridin-2-yl]piperazine, N'-[(1-(cyanomethylcarbonyl)pyrrolidin-2-yl)carbonyl]-N-[3,6-bis(N-ethyl-N-allylamino)pyridin-2-yl]piperazine, N'-[(1-(cyanomethylcarbonyl)pyrrolidin-2-yl)carbonyl]-N-[3-hydroxy-2-pyridinylmethyl)piperazine, N-[(1-methoxymalonylpyrrolidin-2-yl)carbonyl]-N'-[2,6-bis(pyrrolidin-1-yl)pyrimidin-4-yl]piperazine, N-[(1-tert-butoxymalonylpyrrolidin-2-yl)carbonyl]-N'-[3,6-bis(diethylamino)pyridin-2-yl]piperazine.

EXAMPLE 8

0.023 ml of concentrated sulfuric acid are cautiously added to a solution of 4 g of 2,2-dimethylmalonic acid in 30 ml of a 1:2 absolute ethanol/toluene mixture. The reaction mixture is refluxed, distilling the azeotropic water/toluene mixture and adding every few an ethanol/toluene mixture. After 3 hours, the reaction mixture is added with 50 ml of water and extracted with ethyl acetate (3×15 ml). The combined organic extracts are dried over sodium sulfate and solvent is evaporated off under reduced pressure. The residue is purified by silica gel chromatography (eluent 2:1 hexane/AcOEt). 3.3 g of 2,2-dimethylmalonic acid diethyl ester are obtained.

3 g of the obtained diester are dissolved in 20 ml of a 1:1 ethanol/water mixture and added with 0.89 g of potassium hydroxide powder, under stirring. After 3 hours at 60°–70° C., ethanol is distilled off under reduced pressure, then the reaction mixture is added with 20 ml of water and extracted with methylene chloride (2×10 ml). The aqueous phase is acidified with 1N hydrochloric acid and extracted again with methylene chloride (4×10 ml). The second extracts are combined, dried over sodium sulfate and solvent is evaporated off under reduced pressure. 2.1 g of 2,2-dimethylmalonic acid monoethyl ester, a low-melting solid (m.p. 25°–30° C.), are obtained.

EXAMPLE 9

5.4 g of triethylbenzylammonium chloride and a solution of 4 g of diethyl malonate and 4.3 ml of 1,4-dibromobutane in 30 ml of toluene are added to 50 ml of a 50% sodium hydroxide solution in water, at 40° C. and under stirring.

After 5 hours, the reaction mixture is cooled to 0° C. with ice/water and added with 1N hydrochloric acid to acid pH, then it is extracted with ethyl acetate (4×25 ml). The combined organic extracts are repeatedly washed (3×20 ml) with a sodium bicarbonate saturated aqueous solution and dried over sodium sulfate. Finally solvent is evaporated off under reduced pressure, to obtain 3.4 g of 1,1-cyclopentanedicarboxylic acid diethyl ester.

3 g of the obtained diester are dissolved in 30 ml of a 1:1 ethanol/water mixture and added with 0.78 g of potassium hydroxide powder. The reaction mixture is heated to 60° C. for 2 hours, with stirring, then ethanol is distilled off under reduced pressure. The reaction mixture is washed with ethyl acetate (2×10 ml), then added with 1N hydrochloric acid to slightly acid pH and extracted with ethyl acetate (4×15 ml). The second organic extracts are combined and dried over sodium sulfate, solvent is evaporated off under reduced pressure. 2 g of 1,1-cyclopentanedicarboxylic acid monoethyl ester are obtained, which is a low-melting solid.

EXAMPLE 10

A solution of 4.8 ml of ethyl malonyl chloride in 5 ml of acetonitrile is dropped into a solution containing 3 g of 2-aminopyridine, 4.4 g of potassium carbonate and 2.17 g of triethylbenzylammonium chloride in 25 ml of acetonitrile, at room temperature and under stirring. After one hour, the reaction mixture is added with 70 ml of water and repeatedly extracted with ethyl acetate (3×20 ml). The combined organic extracts are dried over sodium sulfate, then solvent is evaporated off under reduced pressure.

The residue (7 g) is purified by silica gel chromatography (eluent 2:1 hexane/AcOEt) to give 4.4 g N-(ethoxymalonyl)-2-aminopyridine.

A solution of 3.7 g of N-(ethoxymalonyl)-2-aminopyridine in 25 ml of acetonitrile, cooled to 0° C. with ice/water, is added with 1.6 ml of 35% sodium hydroxide in water, under stirring. After warming to room temperature, the reaction mixture is left under stirring for 15 more minutes, then 3.5 of N-(carboxymethylcarbonyl)- 2-aminopyridine sodium salt are recovered by filtration, m.p. 195° C.

EXAMPLE 11

A solution of 2.79 ml of ethyl malonyl chloride in 10 ml of acetonitrile is slowly dropped, with stirring and under inert gas atmosphere, into a solution containing 2.55 g of para-toluenesulfonamide, 1.35 g of potassium carbonate and 2.25 g of benzyltriethylammonium chloride in 50 ml of acetonitrile, warmed to 40° C.

The reaction mixture is cooled to room temperature, then, after one hour, solvent is evaporated off under reduced pressure.

The residue is dissolved with 60 ml of ethyl acetate and the resulting organic solution is washed first with a sodium bicarbonate saturated aqueous solution (2×15 ml), then with water (3×15 ml). Then the organic phase is dried over sodium sulfate and solvent is evaporated off under reduced pressure.

2.19 g of N-(ethoxymalonyl)para-toluenesulfonamide are obtained.

13.2 ml of a 1N sodium hydroxide aqueous solution are added to a solution of 1.9 g of N-(ethoxymalonyl)para-toluenesulfonamide in 20 ml of acetonitrile, at room temperature and under stirring. The reaction mixture is heated to 60° C. for one hour, then solvent is evaporated off under reduced pressure and the residue is dissolved with 30 ml of water and repeatedly washed with ethyl acetate (3×5 ml). The aqueous phase is acidified again with 1N hydrochloric acid and extracted with ethyl acetate (3×10 ml). The combined organic extracts are dried over sodium sulfate and solvent is evaporated off under reduced pressure, to obtain 1.6 g of N-(carboxymethylcarbonyl)para -toluenesulfonamide, m.p. 80° C.

EXAMPLE 12

To a solution of 0.4 g of N-(carboxymethylcarbonyl)-2-aminopyridine sodium salt in 20 ml of anhydrous dimethylformamide (DMF), 70 µl of a hydrochloric acid ether solution (2.9M), 0.37 g of 1-ethyl-3-(3-dimethylaminopropyl)carbodiimide hydrochloride and a solution of 0.79 g of N'-[(pyrrolidin-2-yl)carbonyl]-N-[2,6-bis(pyrrolidin-1-yl)pyrimidin-4-yl]piperazine in 25 ml of anhydrous DMF are added, in succession and under inert gas atmosphere. After 3 hours the reaction mixture is added with 100 ml of water and extracted with ethyl acetate (3×20 ml). The combined organic extracts are repeatedly washed with water (3×10 ml) and dried over sodium sulfate. The organic solution is concentrated under reduced pressure and the residue (0.65 g) is purified by silica gel chromatography (eluent 95.5:0.5 methylene chloride/MeOH). 0.5 g of N'-[1-(((pyridin-2-yl)aminocarbonylmethylcarbonyl)pyrrolidin-2-yl)carbonyl]-N-[2,6-bis(pyrrolidin-1-yl)pyrimidin-4-yl)piperazine are obtained, m.p. 182° C.

EXAMPLE 13

Following the procedure described in Example 12, starting from N'-[(pyrrolidin-2-yl)carbonyl]-N-[2,6-bis(pyrrolidin-1-yl)pyrimidin-4-yl]piperazine and the appropriate malonic monoamides prepared according to Example 10, the following N,N'-disubstituted piperazines are prepared:
N'-[(1-(N-methylhydroxylaminocarbonylmethylcarbonyl)pyrrolidin-2-yl)carbonyl]-N-[2,6-bis(pyrrolidin-1-yl)pyrimidin-4-yl]piperazine,
N'-[(1-(aminocarbonylmethylcarbonyl)pyrrolidin-2-yl)carbonyl]-N-[2,6-bis(pyrrolidin-1-yl)pyrimidin-4-yl]piperazine,
N'-[(1-(benzylaminocarbonylmethylcarbonyl)pyrrolidin-2 -yl)carbonyl]-N-[2,6-bis(pyrrolidin-1-yl)pyrimidin-4-yl] piperazine,
N'-[(1-(diethylaminocarbonylmethylcarbonyl)pyrrolidin-2-yl)carbonyl]-N-[2,6-bis(pyrrolidin-1-yl)pyrimidin-4-yl]piperazine,
N'-[(1-(1-piperidinocarbonylmethylcarbonyl)pyrrolidin-2-yl)carbonyl]-N-[2,6-bis(pyrrolidin-1-yl)pyrimidin-4-yl] piperazine,
N'-[(1-(N-morpholinocarbonylmethylcarbonyl)pyrrolidin-2-yl)carbonyl]-N-[2,6-bis(pyrrolidin-1-yl)pyrimidin-4-yl]piperazine,
N'-[(1-(N-(4-thiomorpholino)carbonylmethylcarbonyl)pyrrolidin-2-yl)carbonyl]-N-[2,6-bis(pyrrolidin-1-yl)pyrimidin-4-yl]piperazine,
N'-[(1-(N-(4,5-dithiaazepino)carbonylmethylcarbonyl)pyrrolidin-2-yl)carbonyl]-N-[2,6-bis(pyrrolidin-1-yl)pyrimidin-4-yl]piperazine.

EXAMPLE 14

165 g of methyl 2-chloroacetate are dropped into a solution of 152 g of N-methylpiperazine and 212 ml of triethylamine in 1.5 l of toluene, with stirring and under inert gas atmosphere; then the reaction mixture is heated to 70° C. for 4 hours. After that, the reaction mixture is cooled to room temperature, the resulting precipitate is filtered and washed on the filter with 100 ml of toluene. The resulting organic solution is extracted with water (5×200 ml) and the combined organic extracts are refluxed for about 20 hours, then water is distilled off under reduced pressure. The residue is crystallized from isopropanol, to obtain 168 g of 2-(N-methylpiperazino) acetic acid, m.p. 160°–161° C.

EXAMPLE 15

Following the procedure described in Example 12, starting from N'-[(pyrrolidin-2-yl)carbonyl]-N-[2,6 -bis(pyrrolidin-1-yl)pyrimidin-4-yl]piperazine and from the appropriate 2-substituted acetic acids prepared according to the procedure described in Example 14, the following compounds are prepared:
N'-[(1-(benzylaminomethylcarbonyl)pyrrolidin-2-yl)carbonyl]-N-[2,6-bis(pyrrolidin-1-yl)pirimidin-4-yl]piperazine,
N'-[(1-(diethylaminomethylcarbonyl)pyrrolidin-2-yl)carbonyl]-N-[2,6-bis(pyrrolidin-1-yl)pyrimidin-4-yl]piperazine,
N'-[(1-(1-piperidinomethylcarbonyl)pyrrolidin-2-yl)carbonyl]-N-[2,6-bis(pyrrolidin-1-yl)pyrimidin-4-yl]piperazine,
N'-[(1-(N-morpholinomethylcarbonyl)pyrrolidin-2-yl)carbonyl] -N-[2,6-bis(pyrrolidin-1-yl)pyrimidin-4-yl]piperazine,
(−)-N'-[(1-(N-(4-thiomorpholino)methylcarbonyl)pyrrolidin 2-yl)carbonyl]-N-[2,6-bis(pyrrolidin-1-yl)pyrimidin-4-yl]piperazine, m.p. 225°–226° C., $[\alpha]_D = -16°$ (c=0.2 in DMF),
N'-[(1-(N-(4,5-dithiaazepino)methylcarbonyl)pyrrolidin-2-yl)carbonyl]-N-[2,6-bis(pyrrolidin-1-yl)pyrimidin-4-yl] piperazine,
(−)-N'-[(1-(N-(4-thiamorpholino)methylcarbonyl)pyrrolidin-2-yl)carbonyl]-N-[3,6-bis(diethylamino)pyridin-2-yl]piperazine, hydrochloride m.p. 173°–175° C.,
(−)-N'-[(1-(N-(4-thiamorpholino)methylcarbonyl)pyrrolidin-2-yl)carbonyl]-N-[2,6-bis(pyrrolidin-1-yl)-1,3,5-triazin-4-yl]piperazine, m.p. 205°–207° C.

EXAMPLE 16

A solution of 1 g of N-(carboxymethylcarbonyl)para-toluenesulphonamide in 30 ml of acetonitrile is added, at room temperature and under stirring, with 0.97 g of 1-ethyl-3-(3-dimethylaminopropyl)carbodiimide hydrochloride and 1.56 g of (−)-N'-[pyrrolidin-2-yl)carbonyl]-N-[2,6-bis(pyrrolidin-1-yl)pyrimidin-4-yl]piperazine, in this succession. After 3 hours the reaction mixture is added with 70 ml of water and extracted with ethyl acetate (3×20 ml). The combined organic extracts are washed with water (3×10 ml), dried over sodium sulfate and solvent is evaporated off under reduced pressure. The residue (1.5 g) is purified by silica gel chromatography (eluent 9.5:0.5 AcOEt/MeOH), to obtain 0.95 g of (−)-N'-[(1-(paratoluenesulphonamidocarbonyl-methylcarbonyl)pyrrolidin-2-yl)carbonyl]-N-[2,6-bis(pyrrolidin-1-yl)pyrimidin-2-yl]piperazine, m.p. 170° C., $[\alpha]_D=$ −26.9° (c=2.06 in EtOH).

EXAMPLE 17

A solution of 0.6 g of potassium bicarbonate in 5 ml of water is added to a solution of 2 g of (−)-N'-[(pyrrolidin-2-yl)carbonyl]-N-[2,6-bis(pyrrolidin-1-yl)pyrimidin-4-yl]piperazine in 25 ml of ethyl acetate. The reaction mixture is cooled to 0° C., then a solution of 0.4 ml of acetyl chloride in 2 ml of ethyl acetate is dropped therein, with stirring and under inert gas atmosphere. After 30 minutes at 0° C. the reaction mixture is left to warm to room temperature, to obtain a precipitate melting at 40° C. After 15 minutes the aqueous phase is separated, keeping temperature at 40° C., and the organic phase is washed with water (2×5 ml), dried over sodium sulfate and evaporated under reduced pressure to small volume. From this solution 1.75 g of (−)-N'-[(1-acetylpyrrolidin-2-yl)carbonyl]-N-[2,6-bis(pyrrolidin-1-yl)pyrimidin-4-yl]piperazine crystallize, m.p. 229°–231° C., $[\alpha]_D=$−17° (c=1 in EtOH).

EXAMPLE 18

A solution of 2 g of (−)-N'-[(pyrrolidin-2-yl)carbonyl]-N-[2,6-bis(pyrrolidin-1-yl)pyrimidin-4-yl]piperazine in 20 ml of anhydrous benzene is added with 0.56 g of succinic anhydride and 0.05 g of N,N-dimethylaminopyridine, then the reaction mixture is refluxed for 2 hours. After that, solvent is evaporated off under reduced pressure, to give 3 g of (−)-N'-[(1-(carboxyethylcarbonyl)pyrrolidin-2-yl)carbonyl]-N-[2,6-bis(pyrrolidin-1-yl)pyrimidin-4-yl]piperazine.

The resulting crude product is redissolved in 25 ml of anhydrous ethanol and added with 0.3 ml of concentrated sulfuric acid. The reaction mixture is refluxed for 1 hour, then it is added with 50 ml of a sodium bicarbonate aqueous saturated solution. Ethanol is distilled off under reduced pressure, then the resulting aqueous phase is extracted with ethyl acetate (3×15 ml). The combined organic extracts are washed with a sodium chloride aqueous saturated solution (3×5 ml), dried over sodium sulfate and solvent is evaporated off under reduced pressure. The residue (3 g) is purified by silica gel chromatography (eluent varying AcOEt-AcOEt/MeOH 10:1), to give 2.3 g of (−)-N'-[ (1-(ethoxycarbonylethylcarbonyl)pyrrolidin-2-yl)carbonyl]-N-[2,6-bis(pyrrolidin-1-yl)pyrimidin-4-yl]piperazine, vitreous oil, $[\alpha]_D=$−26° (c=2 in EtOH).

EXAMPLE 19

A solution of 2 g of (−)-N'-[(pyrrolidin-2-yl)carbonyl]-N-[2,6-bis(pyrrolidin-1-yl)pyrimidin-4-yl]piperazine and 0.83 g of powder potassium carbonate in a mixture of 16 ml of acetonitrile and 5 ml of 1,2-dichloroethane is dropped into a mixture of 0.82 ml of ethyl oxalyl chloride in 2 ml of acetonitrile, keeping temperature below 10° C. by means of ice/water. After 30 minutes under stirring, the reaction mixture is added with 70 ml of water, extracted with ethyl acetate (3×15 ml) and dried over sodium sulfate. Solvent is evaporated off under reduced pressure, then the residue is crystallized from ethyl acetate, to obtain 1.8 g of (−)-N'-[(1-(ethyloxalyl)pyrrolidin-2-yl)carbonyl]-N-[2,6-bis(pyrrolidin-1-yl)pyrimidin-4-yl]piperazine, m.p. 197°–199° C., $[\alpha]_D=$−14.9° (c-0.5 in EtOH).

EXAMPLE 20

A solution of (L)-BOC-proline in 60 ml of anhydrous THF, cooled to −10° C. with brine, is added with 6.1 ml of triethylamine and 1 g of 4 A molecular sieve, then, keeping temperature below −5° C., a solution of 4.16 ml of ethyl chloroformate in 5 ml of anhydrous THF is dropped therein. After 30 minute stirring, the reaction mixture is filtered to remove the precipitated triethylammonium chloride and the filtrate is concentrated to 30 ml volume under reduced pressure. The resulting solution is dropped into a suspension of 7.5 g of sodium borohydride in 50 ml of anhydrous THF, cooled to −10° C. with brine. After 2 hours the reaction mixture is added with 200 ml of a sodium dihydrogen phosphate saturated aqueous solution, keeping temperature at 0° C. with ice/water, then it is extracted with ethyl acetate (3×50 ml). The combined organic extracts are repeatedly washed with a sodium chloride saturated aqueous solution (3×30 ml), dried over sodium sulfate and solvent is evaporated off under reduced pressure. The residue is crystallized from hexane, to give 6.1 g of (L)-BOC-prolinol, m.p. 59°–60° C., $[\alpha]_D=$−54.9° (c=0.2 in EtOH).

EXAMPLE 21

0.29 g of carbonyldiimidazole is added in portions to a solution of 0.3 g of (L)-BOC-prolinol in 10 ml of anhydrous THF, cooled to 0° C. with ice/water, with stirring and under inert gas atmosphere, then the reaction mixture is heated to room temperature and stirring is continued for 3 hours. The resulting solution is added with 0.45 g of N-[2,6-bis(pyrrolidin- 1-yl)pyrimidin-4-yl]piperazine, in portions, and stirring is continued for 18 hours. The reaction mixture is added with 40 ml of a sodium dihydrogen phosphate saturated aqueous solution and extracted with ethyl acetate (3×15 ml). The combined organic extracts are dried over sodium sulfate and solvent is evaporated off under reduced pressure. The residue (0.75 g) is purified by silica gel chromatography (eluent 7:3 hexane/AcOEt), to give 0.55 g of (−)-N'-[(1-tert-butoxycarbonyl)pyrrolidin-2-yl)methoxycarbonyl]-N-[2,6-bis(pyrrolidin-1-yl)pyrimidin-4-yl]piperazine, m.p. 147° C., $[\alpha]_D=$−32° (c=0.25 in EtOH).

EXAMPLE 22

0.174 ml of trifluoroacetic acid are dropped into a solution of 100 mg of (−)-N'-[(1-(tert-butoxycarbonyl)pyrrolidin-2-yl)methoxycarbonyl]-N-[2,6-bis(pyrrolidin-1-yl)pyrimidin-4-yl]piperazine in 4 ml of methylene chloride. After about 18 hours, the reaction mixture is added with a 1N sodium hydroxide aqueous solution and it is extracted with methylene chloride (3×3 ml). The combined organic extracts are washed with water (2×2 ml), dried over sodium sulfate and solvent is evaporated off under reduced pressure. The residue is crystallized from 9:1 diisopropyl ether/ethyl acetate, to give 65 mg of (+)-N'-[(pyrrolidin-2-yl)methoxycarbonyl]-N-[2,6-bis(pyrrolidin-1-yl)pyrimidin-4-yl]piperazine, m.p. 137°–138° C., $[\alpha]_D=$8.7° (c=0.23 in EtOH).

EXAMPLE 23

A solution of 0.37 g of 2,2-dimethylmalonic acid monoethyl ester in 10 ml of acetonitrile is added with 0.54 g of 1-ethyl-3-(3-dimethylaminopropyl)carbodiimide hydrochloride, in portions. After 15 minutes the reaction mixture is added with 1 g of (+)-N'-[(pyrrolidin-2-yl)methoxycarbonyl]-N-[2,6-bis(pyrrolidin-1-yl)pyrimidin-4-yl]piperazine with stirring and under inert gas atmosphere. After 3 hours the reaction mixture is added with 100 ml of water and repeatedly extracted with ethyl acetate (3×20 ml). The combined organic extracts are dried over sodium sulfate and solvent is evaporated off under reduced pressure to obtain 1.1 g of (−)-N'-[(1-((2',2'-dimethyl)ethylmalonyl)pyrrolidin-2-yl)methoxycarbonyl]-N-[2,6-bis(pyrrolidin-1-yl)pyrimidin-4-yl]piperazine, m.p. 118°–120° C., $[\alpha]_D = -40.8°$ (c=0.13 in EtOH).

EXAMPLE 24

Following the procedure described in Examples 21, 22 and 23, starting from the appropriate N-substituted piperazines and monoethyl esters of malonic, 2,2-dimethylmalonic, 1,1-cyclopentanedicarboxylic and 1,1-cyclohexanedicarboxylic acids, the following piperazines are prepared:

N'-[(1-ethoxymalonylpyrrolidin-2-yl)methoxycarbonyl]-N-(pyridin-2-yl)piperazine, N'-[(1-ethoxymalonylpyrrolidin-2-yl)methoxycarbonyl]-N-[2,6-bis(diethylamino)pyrimidin-4-yl]piperazine, N'-[(1-ethoxymalonylpyrrolidin-2-yl)methoxycarbonyl]-N-[2,6-bis(allylamino)pyrimidin-4-yl]piperazine, N'-[(1-ethoxymalonylpyrrolidin-2-yl)methoxycarbonyl]-N-[2,6-bis(pyrrolidin-1-yl)pyrimidin-4-yl]piperazine, [(1-ethoxymalonylpyrrolidin-2-yl)methoxycarbonyl]-N-[2,6-bis(diamino)pyrimidin-4-yl]piperazine, N'-[(1-ethoxymalonylpyrrolidin-2-yl)methoxycarbonyl]-N-[2,6-bis(diethylamino)-5-benzoylpyrimidin-4-yl]piperazine, N'-[(1-ethoxymalonylpyrrolidin-2-yl)methoxycarbonyl]-N-[2,6-bis(diethylamino)-5-acetylpyrimidin-4-yl]piperazine, N'-[(1-ethoxymalonylpyrrolidin-2-yl)methoxycarbonyl]-N-[2,6-bis((pyrrolidin-1-yl)-5-acetylpyrimidin-4-yl]piperazine, N'-[(1-ethoxymalonylpyrrolidin-2-yl)methoxycarbonyl]-N-[2,6-bis((pyrrolidin-1-yl)-5-benzoylpyrimidin-4 -yl]piperazine, N'-[(1-ethoxymalonylpyrrolidin-2-yl)methoxycarbonyl]-N-4,6-bis(allylamino)-1,3,5-triazin-2-yl]piperazine, N'-[(1-ethoxymalonylpyrrolidin-2-yl)methoxycarbonyl]-N-[4,6-bis(2-propylamino)-1,3,5-triazin-2-yl]piperazine, N'-[(1-ethoxymalonylpyrrolidin-2-yl)methoxycarbonyl]-N-[4,6-bis(diethylamino)-1,3,5-triazin-2-yl]piperazine, N'-[(1-ethoxymalonylpyrrolidin-2-yl)methoxycarbonyl]-N-[4,6-bis(pyrrolidin-1-yl)-1,3,5-triazin-2-yl]piperazine, N'-[(1-ethoxymalonylpyrrolidin-2-yl)methoxycarbonyl]-N-[3,6-bis(diethylamino)pyridin-2-yl]piperazine, N'-[(1-ethoxymalonylpyrrolidin-2-yl)methoxycarbonyl]-N-[3,6-bis(pyrrolidin-1-yl)pyridin-2-yl]piperazine, N'-[(1-ethoxymalonylpyrrolidin-2-yl)methoxycarbonyl]-N-[3,6-bis(allylamino)pyridin-2-yl]piperazine, N'-[(1-ethoxymalonylpyrrolidin-2-yl)methoxycarbonyl]-N-[3,6-bis(propargylamino)pyridin-2-yl]piperazine, N'-[(1-ethoxymalonylpyrrolidin-2-yl)methoxycarbonyl]-N-[3,6-bis(N-ethyl-N-allylamino)pyridin-2-yl]piperazine, N'-[(1-ethoxymalonylpyrrolidin-2-yl)methoxycarbonyl]-N-(3-hydroxy-2-pyridinylmethyl)piperazine, N'-[(1-((2',2'-dimethyl)ethoxymalonyl)pyrrolidin-2-yl)methoxycarbonyl]-N-(pyridin-2-yl)piperazine, N'-[(1-((2',2'-dimethyl)ethoxymalonyl)pyrrolidin-2-yl)methoxycarbonyl]-N-[2,6-bis(diethylamino)pyrimidin-4-yl]piperazine, N'-[(1-((2',2'-dimethyl)ethoxymalonyl)pyrrolidin-2-yl)methoxycarbonyl]-N-[2,6-bis(allylamino)pyrimidin-4-yl]piperazine, N-[(1-((2',2'-dimethyl)ethoxymalonyl)pyrrolidin-2-yl)methoxycarbonyl]-N-[2,6-bis(diamino)pyrimidin-4-yl]piperazine, N'-[(1-((2',2'-dimethyl)ethoxymalonyl)pyrrolidin-2-yl)methoxycarbonyl]-N-[2,6-bis(diethylamino)-5-benzoylpyrimidin-4-yl]piperazine, N'-[(1-((2',2'-dimethyl)ethoxymalonyl)pyrrolidin-2-yl)methoxycarbonyl]-N-[2,6-bis(diethylamino)-5-acetylpyrimidin-4-yl]piperazine, N'-[(1-((2',2'-dimethyl)ethoxymalonyl)pyrrolidin-2-yl)methoxycarbonyl]-N-[2,6-bis(pyrrolidin-1-yl)-5-acetylpyrimidin-4-yl]piperazine, N'-[(1-((2',2'-dimethyl)ethoxymalonyl)pyrrolidin-2-yl)methoxycarbonyl]-N-[2,6-bis(pyrrolidin-1-yl)-5-benzoylpyrimidin-4-yl]piperazine, N'-[(1-((2',2'-dimethyl)ethoxymalonyl)pyrrolidin-2-yl)methoxycarbonyl]-N-[4,6-bis(allylamino)-1,3,5-triazin-2-yl]piperazine (L)-N'-[(1-((2',2'-dimethyl)ethoxymalonyl)pyrrolidin-2-yl)methoxycarbonyl]-N-[4,6-bis(pyrrolidin-1-yl)-1,3,5-triazin-2-yl]piperazine, m.p. 101°–102° C., N'-[(1-((2',2'-dimethyl)ethoxymalonyl)pyrrolidin-2-yl)methoxycarbonyl]-N-[4,6-bis(2-propylamino)-1,3,5-triazin-2-yl]piperazine, N'-[(1-((2',2'-dimethyl)ethoxymalonyl)pyrrolidin-2-yl)methoxycarbonyl]-N-[4,6-bis(diethylamino)-1,3,5-triazin-2-yl]piperazine N'-[(1-((2',2'-dimethyl)ethoxymalonyl)pyrrolidin-2-yl)methoxycarbonyl]-N-[3,6-bis(diethylamino)pyridin-2-yl]piperazine, N'-[(1-((2',2'-dimethyl)ethoxymalonyl)pyrrolidin-2-yl)methoxycarbonyl]-N-[3,6-bis(pyrrolidin-1-yl)pyridin-2-yl]piperazine, N'-[(1-((2',2'-dimethyl)ethoxymalonyl)pyrrolidin-2-yl)methoxycarbonyl]-N-[3,6-bis(allylamino)pyridin-2-yl]piperazine, N'-[(1-((2',2'-dimethyl)ethoxymalonyl)pyrrolidin-2-yl)methoxycarbonyl]-N-[3,6-bis(propargylamino)pyridin-2-yl]piperazine, N'-[(1-((2',2'-dimethyl)ethoxymalonyl)pyrrolidin-2-yl)methoxycarbonyl]-N-[3,6-bis(N-ethyl-N-allylamino)pyridin-2-yl]piperazine, N'-[(1-((2',2'-dimethyl)ethoxymalonyl)pyrrolidin-2-yl)methoxycarbonyl]-N-[3-hydroxy-2-pyridinylmethyl)piperazine, N'-[(1-(1'-(ethoxycarbonyl)cyclopentane-1'-carbonyl)pyrrolidin-2-yl)methoxycarbonyl]-N-(pyridin-2-yl)piperazine, N'-[(1-(1'-(ethoxycarbonyl)cyclopentane-1'-carbonyl)pyrrolidin-2-yl)methoxycarbonyl]-N-[2,6-bis(diethylamino)pyrimidin-4-yl]piperazine, N'-[(1-(1'-(ethoxycarbonyl)cyclopentane-1'-carbonyl)pyrrolidin-2-yl)methoxycarbonyl]-N-[2,6-bis(allylamino) pyrimidin-4-yl]piperazine, N'-[(1-(1'-(ethoxycarbonyl)cyclopentane-1'-carbonyl)pyrrolidin-2-yl)methoxycarbonyl]-N-[2,6-bis(diamino)pyrimidin-4-yl]piperazine, N'-[(1-(1'-(ethoxycarbonyl)cyclopentane-1'-carbonyl)pyrrolidin-2-yl)methoxycarbonyl]-N-[2,6-bis(diethylamino)-5-benzoylpyrimidin-4-yl]piperazine, N'-[(1-(1'-(ethoxycarbonyl)cyclopentane-1'-carbonyl)pyrrolidin-2-yl)methoxycarbonyl]-N-[2,6-bis(diethylamino)-5-acetylpyrimidin-4-yl]piperazine, N'-[(1-(1'-(ethoxycarbonyl)cyclopentane-1'-carbonyl)pyrrolidin-2-yl)methoxycarbonyl]-N-[2,6-bis(pyrrolidin-1-yl)-5-acetylpyrimidin-4-yl]piperazine, N'-[(1-(1'-(ethoxycarbonyl)cyclopentane-1'-carbonyl)pyrrolidin-2-yl)methoxycarbonyl]-N-[2,6-bis(pyrrolidin-1-yl)-5-benzoylpyrimidin-4-yl]piperazine, N'-[(1-(1'-(ethoxycarbonyl)cyclopentane-1'-carbonyl)pyrrolidin-2-yl)methoxycarbonyl]-N-[4,6-bis(allylamino)- 1,3,5-triazin-2-yl]piperazine, N'-[(1-(1'-(ethoxycarbonyl)cyclopentane-1'-carbonyl)pyrrolidin-2-yl)methoxycarbonyl]-N-[4,6-bis(pyrrolidin-1-yl)-1,3,5-triazin-2-yl]piperazine, N'-[(1-(1'-(ethoxycarbonyl)cyclopentane-1'-carbonyl)pyrrolidin-2-yl)methoxycarbonyl]-N-[4,6-bis(2-propylamino)-1,3,5-triazin-2-yl)piperazine, N'-[(1-(1'-(ethoxycarbonyl)cyclopentane-1'-carbonyl)pyrrolidin-2-yl)methoxycarbonyl]-N-[4,6-bis(diethylamino)-1,3,5-triazin-2-yl]piperazine, N'-[(1-(1'-(ethoxycarbonyl)cyclopentane-1'-carbonyl)pyrrolidin-2-yl)methoxycarbonyl]-N-[3,6-bis(diethylamino)pyridin-2-yl]piperazine, N'-[(1-(1'-(ethoxycarbonyl)cyclopentane-1'-carbonyl)pyrrolidin-2-yl)methoxycarbonyl]-N-[3,6-bis(pyrrolidin-1-yl)pyridin-2-yl]piperazine, N'-[(1-(1'-(ethoxycarbonyl)cyclopentane-1'-carbonyl)pyrrolidin-2-yl)methoxycarbonyl]-N-[3,6-bis(allylamino)pyridin-2-yl]piperazine, N'-[(1-(1'-(ethoxycarbonyl)cyclopentane-1'-carbonyl)pyrrolidin-2-yl)methoxycarbonyl]-N-[3,6-bis(propargylamino)pyridin-2-yl]piperazine, N'-[(1-(1'-(ethoxycarbonyl)cyclopentane-1'-carbonyl)pyrrolidin-2-yl)methoxycarbonyl]-N-[3,6-bis(N-ethyl-N-allylamino)pyridin-2-yl)piperazine, N'-[(1-(1'-(ethoxycarbonyl)cyclopentane-1'-carbonyl)pyrrolidin-2-yl)methoxycarbonyl]-N-(3-hydroxy-2pyridinylmethyl)piperazine, N'-[(1-(1'-(ethoxycarbonyl)cyclohexane-1'-carbonyl)pyrrolidin-2-yl)methoxycarbonyl]-N-(pyridin-2-yl)piperazine, N'-[(1-(1'-(ethoxycarbonyl)cyclohexane-1'-carbonyl)pyrrolidin-2-yl)methoxycarbonyl]-N-[2,6-bis(diethylamino)pyrimidin- 4-yl]piperazine, N'-[(1-(1'-(ethoxycarbonyl)cyclohexane-1'-carbonyl)pyrrolidin-2-yl)methoxycarbonyl]-N-[2,6-bis(allylamino)pyrimidin-4-yl]piperazine, N'-[(1-(1'-(ethoxycarbonyl)cyclohexane-1'-carbonyl)pyrrolidin-2-yl)methoxycarbonyl]-N-[2,6-bis(diamino)pyrimidin-4-yl]piperazine, N'-[(1-(1'-(ethoxycarbonyl)cyclohexane-1'-carbonyl)pyrrolidin-2-yl)methoxycarbonyl]-N-[2,6-bis(diethylamino)-5-benzoylpyrimidin-4-yl]piperazine, N'-[(1-(1'-(ethoxycarbonyl)cyclohexane-1'-carbonyl)pyrrolidin-2-yl)methoxycarbonyl]-N-[2,6-bis(diethylamino)-5-acetylpyrimidin-4-yl]piperazine, N'-[(1-(1'-(ethoxycarbonyl)cyclohexane-1'-carbonyl)pyrrolidin-2-yl)methoxycarbonyl]-N-[2,6-bis(pyrrolidin-1-yl)-5-acetylpyrimidin-4-yl]piperazine, N'-[(1-(1'-(ethoxycarbonyl)cyclohexane-1'-carbonyl)pyrrolidin-2-yl)methoxycarbonyl]-N-[2,6-bis(pyrrolidin-1-yl)-5-benzoylpyrimidin-4-yl]piperazine, N'-[(1-(1'-(ethoxycarbonyl)cyclohexane-1'-carbonyl)pyrrolidin-2-yl)methoxycarbonyl]-N-[4,6-bis(allylamino)-1,3,5-triazin-2-yl]piperazine, N'-[(1-(1'-(ethoxycarbonyl)cyclohexane-1'-carbonyl)pyrrolidin-2-yl)methoxycarbonyl]-N-[4,6-bis(pyrrolidin-1-yl)-1,3,5-triazin-2-yl]piperazine, N'-[(1-(1'-(ethoxycarbonyl)cyclohexane-1'-carbonyl)pyrrolidin-2-yl)methoxycarbonyl]-N-[4,6-bis(2-propylamino)-1,3,5-triazin-2-yl]piperazine, N'-[(1-(1'-(ethoxycarbonyl)cyclohexane-1'-carbonyl)pyrrolidin-2-yl)methoxycarbonyl]-N-[4,6-bis(diethylamino)-1,3,5-triazin-2-yl]piperazine, N'-[(1-(1'-(ethoxycarbonyl)cyclohexane-1'-carbonyl)pyrrolidin-2-yl)methoxycarbonyl]-N-[3,6-bis(diethylamino)pyridin-2-yl]piperazine, N'-[(1-(1'-(ethoxycarbonyl)cyclohexane-1'-carbonyl)pyrrolidin-2-yl)methoxycarbonyl]-N-[3,6-bis(pyrrolidin-1-yl)pyridin-2-yl]piperazine, N'-[(1-(1'-(ethoxycarbonyl)cyclohexane-1'-carbonyl)pyrrolidin- 2-yl)methoxycarbonyl]-N-[3,6-bis(allylamino)pyridin-2-yl]piperazine, N'-[(1-(1'-(ethoxycarbonyl)cyclohexane-1'-carbonyl)pyrrolidin-2-yl)methoxycarbonyl]-N-[3,6-bis(propargylamino)pyridin-2-yl]piperazine, N'-[(1-(1'-(ethoxycarbonyl)cyclohexane-1'-carbonyl)pyrrolidin-2-yl)methoxycarbonyl]-N-[3,6-bis(N-ethyl-N-allylamino)pyridin-2-yl]piperazine, N'-[(1-(1'-(ethoxycarbonyl)cyclohexane-1'-carbonyl)pyrrolidin-2-yl)methoxycarbonyl]-N-[3-hydroxy-2-pyridinylmethyl)piperazine.

EXAMPLE 25

2.08 ml of pivaloyl chloride are dropped into a solution of 4 g of (1-ethoxymalonyl)-1,3-thiazolidine-2-carboxylic acid and 2.36 ml of triethylamine in 40 ml of 1,2-dichloroethane, cooled to −10° C. with brine, with stirring and under inert gas atmosphere. After 15 minutes, keeping temperature always below −5° C., the reaction mixture is added with a solution of 4.89 g of N-[3,6-bis(diethylamino)pyridin-2-yl] piperazine in 4 ml of 1,2-dichloroethane. After 30 minutes the reaction mixture is added with 120 ml of water and the organic phase is separated. The aqueous phase is re-extracted with methylene chloride (3×20 ml), then the combined organic extracts are dried over sodium sulfate and solvent is evaporated off under reduced pressure. The residue is purified by silica gel chromatography (eluent:ethyl ether) and crystallized from 1:1 ethyl ether/ethyl acetate, to obtain 2.66 g of N'-[(1-ethoxymalonylthiazolidin-2-yl)carbonyl]-N-[3,6-bis(diethylamino)pyridin-2-yl]piperazine, m.p. 111°–113° C.

EXAMPLE 26

Following the procedure described in Example 25, by reacting (1-ethoxymalonyl)-1,3-thiazolidine-2-carboxylic acid with an appropriate N-substituted piperazine, the following N,N'-disubstituted piperazines are obtained:

N'-[(1-ethoxymalonylthiazolidin-2-yl)carbonyl I-N-(pyridin-2-yl)piperazine,

N'-[(1-ethoxymalonylthiazolidin-2-yl)carbonyl]-N-[2,6-bis(diethylamino)pyrimidin-4-yl]piperazine, N'-[(1-ethoxymalonylthiazolidin-2-yl)carbonyl]-N-[2,6-bis(allylamino)pyrimidin-4-yl]piperazine, N'-[(1-ethoxymalonylthiazolidin-2-yl)carbonyl]-N-[2,6-bis(pyrrolidin-1-yl)pyrimidin-4-yl]piperazine, m.p. 147°–149° C., N'-[(1-ethoxymalonylthiazolidin-2-yl)carbonyl]-N-[2,6-bis(diamino)pyrimidin-4-yl]piperazine, N'-[(1-ethoxymalonylthiazolidin-2-yl)carbonyl]-N-[2,6-bis(diethylamino)-5-benzoylpyrimidin-4-yl]piperazine, N'-[(1-ethoxymalonylthiazolidin-2-yl)carbonyl]-N-[2,6-bis(diethylamino)-5-acetylpyrimidin-4-yl]piperazine, N'-[(1-ethoxymalonylthiazolidin-2-yl)carbonyl]-N-[2,6-bis(pyrrolidin-1-yl)-5-acetylpyrimidin-4-yl]piperazine, N'-[(1-ethoxymalonylthiazolidin-2-yl)carbonyl]-N-[2,6-bis(pyrrolidin-1-yl)-5-benzoylpyrimidin-4-yl]piperazine, N'-[(1-ethoxymalonylthiazolidin-2-yl)carbonyl]-N-[4,6-bis(allylamino)-1,3,5-triazin-2-yl]piperazine, N'-[(1-ethoxymalonylthiazolidin-2-yl)carbonyl]-N-[4,6-bis(pyrrolidin-1-yl)-1,3,5-triazin-2-yl]piperazine, N'-[(1-ethoxymalonylthiazolidin-2-yl)carbonyl]-N-[4,6-bis(2-propylamino)-1,3,5-triazin-2-yl]piperazine, N'-[(1-ethoxymalonylthiazolidin-2-yl)carbonyl]-N-[4,6-bis(diethylamino)-1,3,5-triazin-2-yl]piperazine, N'-[(1-ethoxymalonylthiazolidin-2-yl)carbonyl]-N-[3,6-bis(pyrrolidin-1-yl)pyridin-2-yl]piperazine, N'-[(1-ethoxymalonylthiazolidin-2-yl)carbonyl]-N-[3,6-bis(allylamino)pyridin-2-yl]piperazine, N'-[(1-ethoxymalonylthiazolidin-2-yl)carbonyl]-N-[3,6-bis(propargylamino)pyridin-2-yl]piperazine, N'-[(1-ethoxymalonylthiazolidin-2-yl)carbonyl]-N-[3,6-bis(N-ethyl-N-allylamino)pyridin-2-yl]piperazine, N'-[(1-ethoxymalonylthiazolidin-2-yl)carbonyl]-N-(3-hydroxy-2-pyridinylmethyl)piperazine, N'-[(1-ethoxymalonylthiazolidin-2-yl)carbonyl]-N-methylpiperazine, m.p. fumarate 126°–129° C.

EXAMPLE 27

13.28 ml of diethyl azadicarboxylate (DEAD) are dropped during 30 minutes into a solution of S(−)-(N-benzylpyrrolidin-2-yl)methanol (6 ml), ditert-butyliminodicarboxylate (11 g) and triphenylphosphine (24 g) in 100 ml of anhydrous THF, maintaining the temperature below 5° C., under stirring and in inert gas atmosphere.

After 5 hours at 0° C., the reaction mixture is worked up by removing the solvent in vacuum. The residue is added with 120 ml of ethyl acetate and repeatedly washed with water (3×60 ml). The organic phase is dried over sodium sulphate and solvent is evaporated off under reduced pressure. The residue (40 g) is purified by silica gel chromatography (eluent 3:1 petroleum ether/diethylether) to obtain 9.8 g of S(−)-[(1-benzylpyrrolidin-2-yl)-N,N-ditert-butoxycarbonyl]methylamine, $^1$H-N.M.R. (200 MHz) in CDCl$_3$ δ1.52 (s,18H); 1,72 (m,4H); 2.21 (m, 1H); 2.86 (m,2H); 3.35 (d,1H); 3.71 (m,2H); 4.11 (d,1H); 7.31 (m,5H).

EXAMPLE 28

5.4 g of S(−)-[(1-benzylpyrrolidin-2-yl)-N,N-ditert-butoxycarbonyl] methylamine are dissolved in 80 ml of methanol and the resulting solution is cooled to ° C. Gaseous hydrogen chloride is bubbled into the reaction mixture for 2hours, then the solvent is evaporated off under reduced pressure, to give 3 g of S(−)-(1-benzylpyrrolidin-2-yl)methylamine hydrochloride, $^1$H-N.M.R. (200 MHz) in D$_2$O δ2.1 (m,3H); 2.51 (m,1H); 3.4 (m,4H); 3.95 (m,1H); 4.4 (d,1H); 4.65 (d,1H); 7.56 (s,5H).

EXAMPLE 29

Into a suspension of S(−)-(1-benzylpyrrolidin-2-yl)methylamine hydrochloride (0.3 g) in 8 ml of THF is dropped under stirring a solution of triethylamine (0.19 ml) in 2 ml of THF. After 15 minutes the precipitate of triethylammonium chloride is filtered off and the reaction mixture is cooled to 0° C., then 0.24 g of N,N'-carbonyldiimidazole are added. The resulting solution, warmed to room temperature, is stirred for 2hours under nitrogen atmosphere, then 0.4 g of N-(2,6-bis(pyrrolidin-1-yl)pyrimidin-4-yl)piperazine are added at once and stirring is continued for 18 hours. The reaction mixture is concentrated under vacuum, diluted with 10 ml of ethyl acetate and whashed with water (3×5 ml). The organic phase is dried over sodium sulphate and the solvent is evaporated under reduced pressure; the residue (0.5 g) is purified by silica gel chromatography (eluent methylene chloride: methanol 95/5) to give 0.35 g of (S)-N-(2,6-bis(pyrrolidin-1-yl)pyrimidin-4-yl)-N'-((1-benzylpyrrolidin-2-yl)methylaminocarbonyl)piperazine, $^1$H-N.M.R. (200 MHz) in D$_6$-benzene δ1.58 (m,12H); 1.92 (m,1H); 2.44 (m,1H); 2.85 (m,1H); 2.98 (d,1H); 3.35 (m,8H); 3.52 (m,4H); 3.72 (m,7H); 4.86 (s,1H); 5.08 (b,1H); 7.18 (m,5H).

EXAMPLE 30

0.18 g of (S)-N-(2,6-bis(pyrrolidin-1-yl)pyrimidin- 4-yl)-N'-((1-benzylpyrrolidin-2-yl)methylaminocarbonyl)piperazine are dissolved in 2ml of methanol, then 100 mg of ammonium formate and 4mg of 0% Pd/C are added and the reaction mixture is refluxed for 6 hours. The suspension is filtered on celite plug and the solvent is evaporated under reduced pressure to give 0.25 g of residue. After purification by silica gel chromatography (eluent methylene chloride:methanol 92/8) 0.13 g of (S)-N-(2,6-bis(pirrolidin-1-yl)pyrimidin-4-yl)-N'-((pirrolidin-2-yl)methylaminocarbonyl)piperazine are obtained, $^1$H-N.M.R. (200 MHz) in CDCl$_3$ δ1.25 (t,3H); 1.45 (s,6H); 1.85 (m,12H); 3.45 (m,21H); 4.2 (q,2H); 4.48 (b,1H); 6.4 (t,1H).

EXAMPLE 31

To a solution of 0.13 g of (S)-N-(2,6-bis(pirrolidin-1-yl)pyrimidin-4-yl)-N'-((pirrolidin-2-yl)methylaminocarbonyl)piperazine in THF (5 ml) are added 90 mg of N-hydroxybenzotriazole, under stirring and in inert gas atmpsphere, then the resulting solution is cooled to −5° C. To the reaction mixture are added 60 mg of 2,2-dimethylmalonic acid monoethylester, 0.036 ml of N-methylmorpholine and 125 mg of 1-ethyl-3-(3-dimethylaminopropyl)carbodiimide hydrochloride, then the temperature is allowed to rise to 25° C. and stirring is continued for 18 hours. The solvent is evaporated under reduced pressure, then the residue is dissolved in 5 ml of ethyl acetate and repeatedly whashed with water (3×5 ml). The organic phase is dried over sodium sulphate and the solvent is evaporated under reduced pressure to give 150 mg of a dark-violet foam, which is purified by silica gel chromatography (eluent methylene chloride:methanol 97/3) obtaining 70 mg of (S)-N-(2,6-bis(pirrolidin-1-yl)pyrimidin-4-yl)-N'-((1-((2',2'-dimethyl)ethoxymalonyl)pirrolidin- 2-yl)methylaminocarbonyl)piperazine, $^1$H-N.M.R. (200 MHz) in CDCl$_3$ δ1.25 (t, 3H); 1.45 (s, 6H); 1.6–2.1 (m, 12H); 3.1–3.6 (m, 20H); 4.2 (q, 2H); 4.45 (m, 1H); 4.85 (s, 1H); 6.45 (t, 1H).

EXAMPLE 32

Following the procedures described in Examples 29, 30 and 31, starting from (N-benzylpyrrolidin-2-yl)methylamine hydrochloride, the appropriate N-substituted piperazines and monoethyl esters of malonic or 2,2-dimethylmalonic acids, the following piperazines are prepared:

N-[(1-ethoxymalonylpyrrolidin-2-yl)methylaminocarbonyl]-N'-[3,6-bis(diethylamino)pyridin-2-yl]piperazine, N-[(1-ethoxymalonylpyrrolidin-2-yl)methylaminocarbonyl]-N'-[2,6-bis(pyrrolidin-2-yl)pyrimidin-4-yl]piperazine, N-[(1-ethoxymalonylpyrrolidin-2-yl)methylaminocarbonyl]-N'-[2,6-bis(pyrrolidin-1-yl)-1,3,5-triazin-4-yl]piperazine, N-[(1-(2',2'-dimethyl)ethoxymalonylpyrrolidin-2-yl)methylaminocarbonyl]-N'-[3,6-bis(diethylamino)pyridin-2-yl]piperazine, N-[(1-(2',2'-dimethyl)ethoxymalonylpyrrolidin-2-yl)methylaminocarbonyl]-N'-[2,6-bis(pyrrolidin-1-yl)-1,3,5-triazin-4-yl]piperazine.

EXAMPLE 33

Following the procedures described in Examples 29, 30 and 31 and substituting in Example 29 carbonyldiimidazole witn thiocarbonildiimidazole, starting from (N-benzylpyrrolidin-2-yl)methylamine hydrochloride, the appropriate N-substituted piperazines and the monoethylester of malonic or 2,2-dimethylmalonic acids, the following N,N'-disubstituted piperazines are prepared:

N-[(1-ethoxymalonylpyrrolidin-2-yl)methylaminothiocarbonyl] -N'-[3,6-bis(diethylamino)pyridin-2-yl]piperazine, N-[(1-ethoxymalonylpyrrolidin-2-yl)methylaminothiocarbonyl]-N'-[2,6-bis(pyrrolidin-2-yl)pyrimidin-4-yl]piperazine, N-[(1-ethoxymalonylpyrrolidin-2-yl)methylaminothiocarbonyl]-N'-[2,6-bis(pyrrolidin-1-yl)-1,3,5-triazin-4-yl]piperazine, N-[(1-(2',2'-dimethyl)ethoxymalonylpyrrolidin-2-yl)methylaminothiocarbonyl]-N'-[3,6-bis(diethylamino)pyridin-2-yl]piperazine, N-[(1-(2',2'-dimethyl)ethoxymalonylpyrrolidin-2-yl)methylaminothiocarbonyl]-N'-[2,6-bis(pyrrolidin-1-yl)pyrimidin-4-yl]piperazine, N-[(1-(2',2'-dimethyl)ethoxymalonylpyrrolidin-2-yl)methylaminothiocarbonyl]-N'-[2,6-bis(pyrrolidin-1-yl)-1,3,5-triazin-4-yl]piperazine.

EXAMPLE 34

Following the procedures described in Examples 21, 22 and 23, starting from the appropriate N-substituted piperazines and monoethylesters of malonic or 2,2-dimethylmalonic acids, and substituting in Example 21 carbonyldiimidazole with thiocarbonyldiimidazole, the following piperazines are obtained:

N-[(1-ethoxymalonylpyrrolidin-2-yl)methoxythiocarbonyl] -N'-[3,6-bis(diethylamino)pyridin-2-yl]piperazine, N-[(1-ethoxymalonylpyrrolidin-2-yl)methoxythiocarbonyl] -N'-[2,6-bis(pyrrolidin-2-yl)pyrimidin-4-yl]piperazine, N-[(1-ethoxymalonylpyrrolidin-2-yl)methoxythiocarbonyl] -N'-[2,6-bis(pyrrolidin-1-yl)-1,3,5-triazin-4-yl]piperazine, N-[(1-(2',2'-dimethyl)ethoxymalonylpyrrolidin-2-yl)methoxythiocarbonyl]-N'-[3,6-bis(diethylamino)pyridin- 2-yl]piperazine, (L)-N-[(1-(2',2'-dimethyl)ethoxymalonylpyrrolidin-2-yl)methoxythiocarbonyl]-N'-[2,6-bis(pyrrolidin-1-yl)pyrimidin-4-yl]piperazine, m.p. 123°–124° C., N-[(1-(2',2'-dimethyl)ethoxymalonylpyrrolidin-2-yl)methoxythiocarbonyl]-N'-[2,6-bis(pyrrolidin-1-yl)-1,3, 5-triazin-4-yl]piperazine.

EXAMPLE 35

Following the procedures described in Examples 21, 22and 23, starting from the appropriate N-substituted piperazines and (4-thiamorpholin-1-yl), morpholin-1-yl or (4-methylpiperazin-1-yl)acetic acids, the following piperazines are prepared:

N-[(1-((4-thiamorpholin-1-yl)methylcarbonyl)pyrrolidin-2-yl)methoxycarbonyl]-N'-[3,6-bis(diethylamino)pyridin-2-yl]piperazine, N-[(1-((4-thiamorpholin-1-yl)methylcarbonyl)pyrrolidin-2-yl)methoxycarbonyl]-N'-[2,6-bis(pyrrolidin-2 -yl)pyrimidin-4-yl]piperazine, N-[(1-((4-thiamorpholin-1-yl)methylcarbonyl)pyrrolidin-2-yl)methoxycarbonyl]-N'-[2,6-bis(pyrrolidin-1-yl)-1,3,5-triazin-4-yl]piperazine, N-[(1-((morpholin-1-yl)methylcarbonyl)pyrrolidin-2-yl)methoxycarbonyl]-N'-[3,6-bis(diethylamino)pyridin-2 -yl]piperazine, N-[(1-((morpholin-1-yl)methylcarbonyl)pyrrolidin-2-yl)methoxycarbonyl]-N'-[2,6-bis(pyrrolidin-1-yl)pyrimidin-4-yl]piperazine, N-[(1-((morpholin-1-yl)methylcarbonyl)pyrrolidin-2-yl)methoxycarbonyl]-N'-[2,6-bis(pyrrolidin-1-yl)-1,3,5 -triazin-4-yl]piperazine, N-[(1-((4-methylpiperazin-1-yl)methylcarbonyl)pyrrolidin-2-yl)methoxycarbonyl]-N'-[3,6-bis(diethylamino)pyridin-2-yl]piperazine, N-[(1-((4-methylpiperazin-1-yl)methylcarbonyl)pyrrolidin-2-yl)methoxycarbonyl]-N'-[2,6-bis(pyrrolidin-1-yl)pyrimidin-4-yl]piperazine, N-[(1-((4-methylpiperazin-1-yl)methylcarbonyl)pyrrolidin-2-yl)methoxycarbonyl]-N'-[2,6-bis(pyrrolidin-1-yl)-1,3, 5-triazin-4-yl]piperazine, N-[(t-((piperidin-1-yl)methylcarbonyl)pyrrolidin-2-yl)-methoxycarbonyl]-N'-[3,6-bis(diethylamino)pyridin-2 -yl]piperazine, N-[(1-((piperidin-1-yl)methylcarbonyl)pyrrolidin-2-yl)methoxycarbonyl]-N'-[2,6-bis(pyrrolidin-1-yl)pyrimidin-4-yl]piperazine, N-[(1-((piperidin-1-yl)methylcarbonyl)pyrrolidin-2-yl)methoxycarbonyl]-N'-[2,6-bis(pyrrolidin-1-yl)-1,3,5 -triazin-4-yl]piperazine.

We claim:
1. Compounds of formula (I):

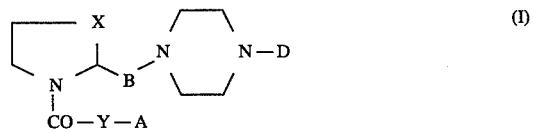

the single enantiomeric and diastereoisomeric forms thereof, the racemic mixtures thereof and the salts thereof with pharmaceutically acceptable acids and bases, wherein:

X is $CH_2$ or S;

B is a —CO—, —$CH_2$—, —$CH_2OCO$—, —$CH_2OCS$—, —$CH_2NHCO$—, or —$CH_2NHCS$— group;

D is a benzyl group which can optionally be substituted by hydroxy and/or $C_1$–$C_6$ alkoxy groups; benzhydryl optionally substituted by halogen atoms; phenyl optionally substituted by halogen atoms; (3-hydroxy-2 -pyridyl)methyl; 5- or 6-membered heterocycle with 1–3 nitrogen atoms, which can possibly be substituted by 1 or 2amino groups, mono-$C_1$–$C_6$-alkylamino, mono-$C_3$–$C_7$-alkenyl- or mono-$C_3$–$C_7$-alkinylamino, di-$C_1$–$C_6$-alkylamino, ($C_1$–$C_6$)alkyl($C_3$–$C_7$)alkenylamino, piperidin-1-yl, morpholin-4-yl, pyrrolidin-1-yl;

Y is a single carbon-carbon bond or a group of formula

—$CH_2CH_2$—; —$CH_2$—$CH_2$—$CH_2$—; —(CRaRb)— wherein Ra and Rb are hydrogen, $C_1$–$C_3$ alkyl or, taken together with the carbon atom which they are linked to, form a $C_3$-$C_6$ cycloalkyl group;

A is selected from the group consisting of:
a) a free or salified carboxy group, which can possibly be esterified with $C_1$-$C_4$ alkyl alcohols, or amide, sulfonamide or hydroxyamido derivatives thereof, respectively of formulae CONRcRd, CONHSO$_2$Rf and CONRgOH, wherein Rc and Rd, which can be the same or different, are hydrogen, $C_1$-$C_6$ alkyl, benzyl, ortho-, meta- or para-aminopyridino, or, taken together with the nitrogen atom, form a pyrrolidino, piperidino, morpholino, 4-thiomorpholino, 4,5-dithiaazepino, $C_1$-$C_4$ -4-alkylpiperazino, imidazolyl group; Rf is $C_1$-$C_4$-alkyl, trihalomethyl, tolyl or phenyl, optionally substituted by halogen atoms; Rg is H or $C_1$-$C_4$-alkyl;
b) $C_1$-$C_3$-alkyl;
c) NRcRd, where in Rc and Rd are as defined above;
d) —CO—Rh, wherein Rh is $C_1$-$C_2$ alkyl optionally substituted by $C_5$-$C_6$ cycloalkyl or phenyl groups;
e) when Y is different from a bond, A can also be —CN; enantiomers and/or diastereoisomers thereof, both isolated and in the various mixtures thereof, and the salts thereof with pharmaceutically acceptable acids and bases.

2. Compounds according to claim 1, wherein D is selected from the group consisting of 2-pyridyl, (3-hydroxy- 2-pyridinyl)methyl, [2,6-bis(diethylamino)-4-pyrimidinyl], [2,6-bis(allylamino)-4-pyrimidinyl], [2,6-bis(amino)-4-pyrimidinyl], [2,6-bis(pyrrolidin-1-yl)-4-pyrimidinyl], [2,6-bis(diethylamino)-5-benzoyl-4-pyrimidinyl], [2,6-bis(diethylamino)-5-acetyl-4-pyrimidinyl], [2,6-bis(pyrrolidin-1-yl)-5-acetyl-4-pyrimidinyl], [2,6-bis(pyrrolidin-1-yl)-5-benzoyl-4-pyrimidinyl], [4,6-bis(2-allylamino)-1,3,5-triazin-2-yl], [4,6-bis(2-propylamino)-1,3,5-triazin-2-yl], [4,6 -bis(diethylamino)-1,3,5-triazin-2-yl], [4,6-bis(pyrrolidin-1-yl)-1,3,5-triazin-2-yl], [3,6-bis(diethylamino)-pyridin-2-yl], [3,6-bis(pyrrolidin-1-yl)-pyridin-2-yl], [3,6-bis(allylamino)-pyridin-2-yl], [3,6-bis(propargylamino)-pyridin-2-yl], [3,6-bis(N-ethyl-N-allylamino)-pyridin-2-yl].

3. Compounds according to claim 1, wherein B is a —CO—, —CH$_2$—O—CO—, —CH$_2$NHCO— or —CH$_2$—NHCS— group; D is an heterocycle selected from the group consisting of [2,6-bis(pyrrolidin-1-yl)-4-pyrimidinyl], [4,6-bis(pyrrolidin-1-yl)-1,3,5-triazin-2-yl]and [3,6-bis(diethylamino)-pyridin-2-yl]; y is —(CRaRb)—, wherein Ra, which is the same as Rb, is hydrogen or methyl or Ra and Rb, taken together with the carbon atom which they are linked to, are cyclopentyl or cyclohexyl; A is an ethoxycarbonyl, methane- or tolyl-sulphonamido, pyridin-2-yl-aminocarbonyl, N-methyl-hydroxylaminocarbonyl, N-(4,5-dithiaazepino)carbonyl, N-(4,5-dithiaazepino), 1-oxoethane, 1-oxopropane group.

4. Compounds according to claim 1, wherein X is $CH_2$.

5. Pharmaceutical compositions comprising one compound according to claim 1 as the active ingredient together with at least one pharmaceutically acceptable carrier or excipient.

6. A method of preparing a medicament, comprising incorporating at least one compound according to claim 1 into the form of a medicament having antiasthmatic and antiinflammatory activities on the respiratory tract.

7. A compound of formula (Ia):

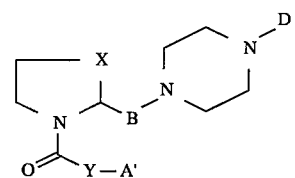

(Ia)

in which X is $CH_2$ or S; B is a —CO—, —CH$_2$—, —CH$_2$OCO—, —CH$_2$OCS—, —CH$_2$NHCO—, or —CH$_2$NHCS— group; D is a benzyl group which can optionally be substituted by hydroxy and/or $C_1$-$C_6$ alkoxy groups; benzhydryl optionally substituted by halogen atoms; phenyl optionally substituted by halogen atoms; (3-hydroxy-2-pyridyl)methyl; 5- or 6-membered heterocycle with 1–3 nitrogen atoms, which can possibly be substituted by 1 or 2 amino groups, mono-$C_1$-$C_6$-alkylamino, mono-$C_3$-$C_7$-alkenyl- or mono-$C_3$-$C_7$-alkinylamino, di-$C_1$-$C_6$-alkylamino, ($C_1$-$C_6$)alkyl($C_3$-$C_7$)alkenylamino, piperidin-1-yl, morpholin-4-yl or pyrrolidin-1-yl; Y is a bond and A' is a halogen atom, selected from the group consisting of chlorine, bromine and iodine.

* * * * *